(12) United States Patent
Takanashi et al.

(10) Patent No.: US 11,215,928 B2
(45) Date of Patent: Jan. 4, 2022

(54) COMPOSITION FOR RESIST UNDERLAYER FILM FORMATION, RESIST UNDERLAYER FILM AND METHOD FOR FORMING THE SAME, AND PRODUCTION METHOD OF A PATTERNED SUBSTRATE

(71) Applicant: JSR CORPORATION, Tokyo (JP)

(72) Inventors: Kazunori Takanashi, Tokyo (JP); Hiroki Nakatsu, Tokyo (JP); Kazunori Sakai, Tokyo (JP); Ichihiro Miura, Tokyo (JP)

(73) Assignee: JSR CORPORATION, Tokyo (JP)

( * ) Notice: Subject to any disclaimer, the term of this patent is extended or adjusted under 35 U.S.C. 154(b) by 295 days.

(21) Appl. No.: 16/354,344

(22) Filed: Mar. 15, 2019

(65) Prior Publication Data

US 2019/0212650 A1    Jul. 11, 2019

Related U.S. Application Data

(63) Continuation of application No. PCT/JP2017/032592, filed on Sep. 8, 2017.

(30) Foreign Application Priority Data

Sep. 16, 2016  (JP) .............................. JP2016-181542
Mar. 21, 2017  (JP) .............................. JP2017-054209

(51) Int. Cl.
| | |
|---|---|
| G03F 7/11 | (2006.01) |
| C07D 265/16 | (2006.01) |
| G03F 7/09 | (2006.01) |
| H01L 21/027 | (2006.01) |
| C07D 413/14 | (2006.01) |
| C09D 165/00 | (2006.01) |
| G03F 7/16 | (2006.01) |
| C09D 161/12 | (2006.01) |

(52) U.S. Cl.
CPC .............. *G03F 7/11* (2013.01); *C07D 265/16* (2013.01); *C07D 413/14* (2013.01); *C09D 165/00* (2013.01); *G03F 7/094* (2013.01); *G03F 7/162* (2013.01); *G03F 7/168* (2013.01); *H01L 21/0273* (2013.01); *C09D 161/12* (2013.01); *H01L 21/0271* (2013.01)

(58) Field of Classification Search
CPC ........................................................ G03F 7/11
See application file for complete search history.

(56) References Cited

U.S. PATENT DOCUMENTS

| | | | |
|---|---|---|---|
| 7,476,476 B2 | 1/2009 | Suwa | |
| 8,975,318 B2 * | 3/2015 | Tietze | C08G 59/621 524/199 |
| 9,261,790 B2 | 2/2016 | Someya et al. | |
| 9,797,620 B2 | 10/2017 | Matsugi et al. | |
| 2006/0159839 A1* | 7/2006 | Suwa | C08G 73/101 427/66 |
| 2015/0011092 A1 | 1/2015 | Someya et al. | |
| 2017/0159963 A1 | 6/2017 | Matsugi et al. | |
| 2020/0004149 A1* | 1/2020 | Lee | C08G 73/1085 |

FOREIGN PATENT DOCUMENTS

| | | | |
|---|---|---|---|
| JP | 2004-177668 A | | 6/2004 |
| JP | 2011075987 A | * | 4/2011 |
| TW | 200502320 A | | 1/2005 |
| TW | 201000536 A | | 1/2010 |
| TW | 201348886 A | | 12/2013 |
| TW | 201817722 A | | 5/2018 |
| WO | WO 2013/115097 A1 | | 8/2013 |
| WO | WO-2015115097 A1 | | 8/2015 |

(Continued)

OTHER PUBLICATIONS

English translation of WO 2018/016614 A1, machine generated from on patentscope on WIPO IP Portal on Mar. 12, 2021, 233 pages (Year: 2021).*
Japanese patent application 2016/143659 filed on Jul. 21, 2016 in PCT/JP2017/026412 (publication WO2018/016614 as a priority document therefore and obtained from Global Dossier website. (Year: 2016).*
English translation of JP 2011075987 a obtained from J-PlatPat, 100 pages on Mar. 13, 2021. (Year: 2021).*
International Search Report dated Dec. 12, 2017 in PCT/JP2017/032592, 5 pages (with English translation).
Written Opinion of the International Searching Authority dated Dec. 12, 2017 in PCT/JP2017/032592, 7 pages (with English translation).
Combined Office Action and Search Report dated Apr. 29, 2021 in Taiwanese Patent Application No. 106131372 (with English translation), 28 pages.

(Continued)

*Primary Examiner* — Duane Smith
*Assistant Examiner* — Nicholas E Brown
(74) *Attorney, Agent, or Firm* — Element IP, PLC

(57) ABSTRACT

A composition for resist underlayer film formation contains: a first compound including at least one oxazine structure fused to an aromatic ring; and a solvent. The first compound preferably includes a partial structure represented by formula (1). In formula (1), $R^2$ to $R^5$ each independently represent a hydrogen atom or a monovalent organic group having 1 to 20 carbon atoms; $Ar^1$ represents a group obtained by removing (n+3) or (n+2) hydrogen atoms on the aromatic ring from an arene having 6 to 20 carbon atoms; $R^6$ represents a hydroxy group, a halogen atom, a nitro group or a monovalent organic group having 1 to 20 carbon atoms; and n is an integer of 0 to 9.

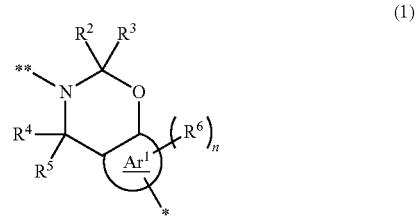

(1)

8 Claims, 1 Drawing Sheet

(56) References Cited

FOREIGN PATENT DOCUMENTS

WO     WO-2018016614 A1 *   1/2018  ............... G03F 7/20
WO     WO-2019054625 A1 *   3/2019  ........... C09D 179/08

OTHER PUBLICATIONS

Viktoria V. Petrakova et al, "Benzoxazine Monomers and Polymers Based on 3,3'-Dichloro-4,4'-Diaminodiphenylmethane: Synthesis and Characterization", Polymers, 13, 1421, 2021, pp. 1-19.

Office Action dated Mar. 2, 2021 in Japanese Patent Application No. 2018-539694 (with English translation), 4 pages.

Combined Office Action and Search Report dated Oct. 28, 2021 in Taiwanese Patent Application No. 106131372 (with English translation), received Nov. 11, 2021, 10 pages.

\* cited by examiner

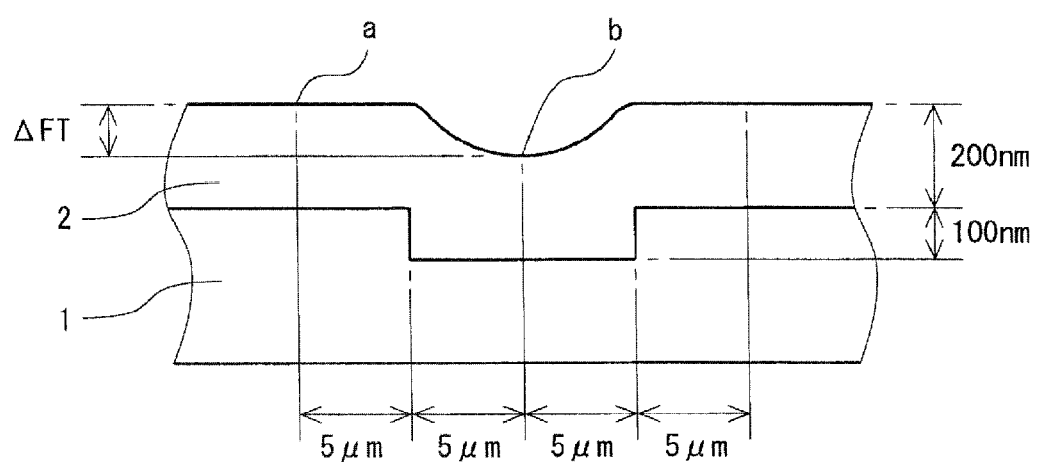

COMPOSITION FOR RESIST UNDERLAYER FILM FORMATION, RESIST UNDERLAYER FILM AND METHOD FOR FORMING THE SAME, AND PRODUCTION METHOD OF A PATTERNED SUBSTRATE

CROSS-REFERENCE TO RELATED APPLICATIONS

The present application is a continuation application of International Application No. PCT/JP2017/032592, filed Sep. 8, 2017, which claims priority to Japanese Patent Application No. 2016-181542, filed Sep. 16, 2016 and to Japanese Patent Application No. 2017-054209, filed Mar. 21, 2017. The contents of these applications are incorporated herein by reference in their entirety.

BACKGROUND OF THE INVENTION

Field of the Invention

The present invention relates to a composition for resist underlayer film formation, a resist underlayer film and a method for forming the same, and a production method of a patterned substrate.

Discussion of the Background

In Manufacturing semiconductor devices, multilayer resist processes have been employed for attaining a high degree of integration. In these processes, a composition for resist underlayer film formation is first applied directly or indirectly on a substrate, and then a coating film thus obtained is heated, thereby forming a resist underlayer film. A resist pattern is formed by using a resist composition directly or indirectly on the resist underlayer film Subsequently, the resist underlayer film is etched by using the resist pattern as a mask, and the substrate is further etched by using the resultant resist underlayer film pattern as a mask, thereby enabling a desired pattern to be formed on the substrate. Accordingly, a patterned substrate can be obtained. The resist underlayer film for use in such a multilayer resist process is required to have general characteristics such as solvent resistance and etching resistance.

In addition, there are increasing cases of pattern formation on a substrate having multiple types of trenches, particularly trenches with aspect ratios that are different from one another. In these cases, the composition for resist underlayer film formation is required to sufficiently fill these trenches, and to provide superior flatness.

To meet the demands as described above, structures of polymers, etc. contained in the composition for resist underlayer film formation, and functional groups included in the polymers have been extensively investigated (see Japanese Unexamined Patent Application, Publication No. 2004-177668).

SUMMARY OF THE INVENTION

According to an aspect of the present invention, a composition for resist underlayer film formation contains: a first compound including at least one oxazine structure fused to an aromatic ring; and a solvent.

According to another aspect of the present invention, a resist underlayer film is formed from the composition for resist underlayer film formation.

According to further aspect of the present invention, a method for resist underlayer film formation includes applying the composition for resist underlayer film formation directly or indirectly on a substrate to obtain a coating film. The coating film is heated.

According to further aspect of the present invention, a production method of a patterned substrate includes applying the composition for resist underlayer film formation directly or indirectly on a substrate to obtain a coating film. The coating film is heated to obtain a resist underlayer film. A resist pattern is formed directly or indirectly on the resist underlayer film. Etching is carried out with the resist pattern used as a mask.

BRIEF DESCRIPTION OF THE DRAWINGS

FIGURE is a schematic cross sectional view for illustrating an evaluation method of flatness.

DESCRIPTION OF EMBODIMENTS

According to one embodiment of the invention, a composition for resist underlayer film formation contains: a first compound having an oxazine structure fused to an aromatic ring; and a solvent.

According to another embodiment of the invention, a resist underlayer film is formed from a composition for resist underlayer film formation, the composition containing: a first compound having at least one oxazine structure fused to an aromatic ring; and a solvent.

According to yet another embodiment of the invention, a method for resist underlayer film formation includes: applying a composition for resist underlayer film formation directly or indirectly on a substrate; and heating a coating film obtained by the applying of the composition, the composition containing: a first compound comprising at least one oxazine structure fused to an aromatic ring; and a solvent.

According to still another embodiment of the invention, a production method of a patterned substrate includes: applying a composition for resist underlayer film formation directly or indirectly on a substrate; heating a coating film obtained by the applying of the composition; forming a resist pattern directly or indirectly on a resist underlayer film obtained by the heating of the coating film; and carrying out etching with the resist pattern used as a mask, the composition containing: a first compound comprising at least one oxazine structure fused to an aromatic ring; and a solvent.

The composition for resist underlayer film formation of the one embodiment of the present invention is capable of forming a resist underlayer film having superior flatness, and being superior in both solvent resistance and etching resistance. The resist underlayer film of the another embodiment of the present invention has superior flatness, and is superior in both solvent resistance and etching resistance. The method for resist underlayer film formation of the yet another embodiment of the invention enables a resist underlayer film having superior flatness to be formed. The production method of a patterned substrate of the still another embodiment of the invention enables a substrate having a favorable pattern configuration to be obtained by using a superior resist underlayer film formed as described above. Therefore, these can be suitably used for manufacture, etc., of semiconductor devices in which further progress of microfabrication is expected in the future. Hereinafter, embodiments of the present invention will be described in detail.

Composition for Resist Underlayer Film Formation

The composition for resist underlayer film formation of an embodiment of the invention contains: a first compound having an oxazine structure fused to an aromatic ring (hereinafter, may be also referred to as "(A) compound" or "compound (A)"); and a solvent (hereinafter, may be also referred to as "(B) solvent" or "solvent (B)"). The composition for resist underlayer film formation may contain as a favorable component, an acid generating agent (hereinafter, may be also referred to as "(C) acid generating agent" or "acid generating agent (C)") and/or a crosslinking agent (hereinafter, may be also referred to as "(D) crosslinking agent" or "crosslinking agent (D)"), and may further contain other optional component within a range not leading to impairment of the effects of the present invention. Hereinafter, each component is explained.

(A) Compound

The compound (A) has an oxazine structure fused to an aromatic ring. The "oxazine structure" as referred to herein may include a ring structure that includes a linkage of atoms of —O—C—N—C—C—C—, a ring structure that includes a linkage of atoms of —O—N—C—C—C—C—, or a ring structure that includes a linkage of atoms of —O—C—C—N—C—C—. The "oxazine structure fused to an aromatic ring" as referred to herein means the oxazine structure that shares two carbon atoms with an aromatic ring. As the oxazine structure, the ring structure that includes a linkage of atoms of —O—C—N—C—C—C— is preferred. Preferably, the oxazine structure shares two carbon atoms with the aromatic ring, and the ring structure of the oxazine structure includes the linkage of atoms of —O—C—N—C—C—C—. In regard to the oxazine structure including the ring structure that includes a linkage of atoms of —O—C—N—C—C—C—, provided that the O atom resides at position 1 and the N atom resides at position 3, the oxazine structure that shares two carbon atoms with the aromatic ring at positions 5 and 6 is preferred. Examples of the aromatic ring include aromatic rings having 6 to 20 carbon atoms such as a benzene ring, a naphthalene ring, an anthracene ring, a phenanthrene ring and a tetracene ring, and the like. Of these, a benzene ring and a naphthalene ring are preferred. One, or two or more types of the compound (A) may be contained.

Due to containing the compound (A), the composition for resist underlayer film formation is capable of forming a film having superior flatness and being superior in both solvent resistance and etching resistance. Although not necessarily clarified and without wishing to be bound by any theory, the reason for the aforementioned effects achieved by the composition for resist underlayer film formation due to the constitution described above can be inferred as in the following, for example. Specifically, the compound (A) has a structure (oxazine structure fused to an aromatic ring) constituted with an aromatic ring and the oxazine structure fused to this aromatic ring. Crosslinking between molecules by way of the oxazine structure of the compound (A) is enabled, and volumic contraction in the crosslinking is considered to be small. Therefore, the composition for resist underlayer film formation is believed to result in improved flatness. In addition, the compound (A) has an aromatic ring in the compound, and a proportion occupied by the aromatic ring is large even after the crosslinking; therefore, the formed film is considered to have solvent resistance and etching resistance both being improved. It is to be noted that the compound (A) preferably has a plurality of the oxazine structures.

The compound (A) preferably has a partial structure (hereinafter, may be also referred to as "partial structure (I)") represented by the following formula (1).

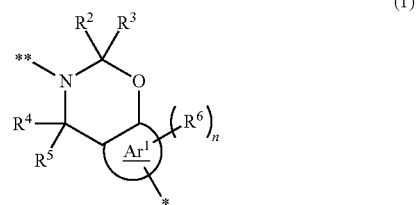

In the above formula (1), $R^2$ to $R^5$ each independently represent a hydrogen atom or a monovalent organic group having 1 to 20 carbon atoms; $Ar^1$ represents a group obtained by removing (n+3) or (n+2) hydrogen atoms on the aromatic ring from an arene having 6 to 20 carbon atoms; $R^6$ represents a hydroxy group, a halogen atom, a nitro group or a monovalent organic group having 1 to 20 carbon atoms; n is an integer of 0 to 9, wherein in a case in which n is no less than 2, a plurality of $R^6$s may be identical or different, and two or more of the plurality of $R^6$s may taken together represent a ring structure having 4 to 20 ring atoms together with the carbon chain to which the two or more of the plurality of $R^6$s bond; and * and ** each independently denote a bonding site to a part other than the partial structure represented by the formula (1) in the first compound.

The monovalent organic group having 1 to 20 carbon atoms which may be represented by $R^2$ to $R^6$ is exemplified by: a monovalent hydrocarbon group having 1 to 20 carbon atoms; a group (α) that includes a divalent hetero atom-containing group between two adjacent carbon atoms of the hydrocarbon group having 1 to 20 carbon atoms, or between carbon atoms to which the hydrocarbon group having 1 to 20 carbon atoms and $R^2$ to $R^6$ bond; a group obtained from the hydrocarbon group having 1 to 20 carbon atoms or the group (α) by substituting a part or all of hydrogen atoms included therein with a monovalent hetero atom-containing group; and the like.

Examples of the monovalent hydrocarbon group having 1 to 20 carbon atoms include chain hydrocarbon groups e.g., alkyl groups such as a methyl group, an ethyl group, a propyl group, a butyl group and a pentyl group; alkenyl groups such as an ethenyl group, a propenyl group and a butenyl group; and alkynyl groups such as an ethynyl group, a propynyl group and a butynyl group, alicyclic hydrocarbon group, e.g., cycloalkyl groups such as a cyclopentyl group and a cyclohexyl group; cycloalkenyl groups such as a cyclopropenyl group, a cyclopentenyl group and a cyclohexenyl group; bridged cyclic hydrocarbon groups such as a norbornyl group and an adamantyl group, and aromatic hydrocarbon group, e.g., aryl groups such as a phenyl group, a tolyl group, a xylyl group and a naphthyl group; and aralkyl groups such as a benzyl group, a phenethyl group and a naphthylmethyl group; and the like.

Examples of the divalent hetero atom-containing group include —CO—, —CS—, —NH—, —O—, —S—, and groups obtained by combining the same, and the like.

Examples of the group (α) that includes a divalent hetero atom-containing group between two adjacent carbon atoms of the hydrocarbon group or between carbon atoms to which the hydrocarbon group and $R^2$ to $R^6$ bond include:

hetero atom-containing chain groups such as an oxoalkyl group, a thioalkyl group, an alkylaminoalkyl group, an alkoxyalkyl group and an alkylthioalkyl group;

aliphatic heterocyclic groups such as an oxocycloalkyl group, a thiocycloalkyl group, an azacycloalkyl group, an oxacycloalkyl group, a thiacycloalkyl group, an oxocycloalkenyl group and an oxathiacycloalkyl group;

aromatic heterocyclic groups. e.g., heteroaryl groups such as a pyrrolyl group, a pyridyl group, a quinolyl group, an isoquinolyl group, a furyl group, a pyranyl group, a thienyl group and a benzothiophenyl group; and the like.

Examples of the monovalent hetero atom-containing group include a hydroxy group, a sulfanyl group, a cyano group, a nitro group, a halogen atom, and the like.

$R^2$ to $R^5$ represents preferably a hydrogen atom or an alkyl group, and more preferably a hydrogen atom.

Examples of the arene having 6 to 20 carbon atoms that gives $Ar^1$ include benzene, naphthalene, anthracene, phenanthrene, tetracene, pyrene, triphenylene, perylene, and the like. Of these, benzene and naphthalene are preferred, and benzene is more preferred.

$R^6$ represents preferably a hydroxy group, a halogen atom or a monovalent organic group having 1 to 20 carbon atoms, more preferably a monovalent hydrocarbon group, and still more preferably an alkyl group.

In the above formula, n is preferably 0 to 3, more preferably 0 to 2, still more preferably 0 or 1, and particularly preferably 0.

The ring structure having 6 to 20 ring atoms which may be taken together represented by two or more of a plurality of $R^6$s together with the atom chain to which the two or more of the plurality of $R^6$s bond include alicyclic structures such as a cyclohexane structure and a cyclohexene structure, aliphatic heterocyclic structures such as an azacyclohexane structure and an azacyclohexene structure, aromatic heterocyclic structures such as a pyridine structure, and the like.

When $Ar^1$ in the above formula (1) is a group derived from benzene, in the partial structure (I), a position of —O— of the oxazine structure with respect to the bonding site denoted by "*" in the formula (1) may be any of the para-position, the meta-position and the ortho-position of the benzene ring, but in light of ease in synthesis of the compound (A), the para-position is preferred. Alternatively, when $Ar^1$ is a group derived from naphthalene, and the bonding site denoted by "*" in the formula (1) is the position 2 of the naphthalene ring, a position of —O— of the oxazine structure is preferably the position 6 of the naphthalene ring.

A group (hereinafter, may be also referred to as "group (I-A)") provided by bonding of $R^1$ that is the monovalent organic group having 1 to 20 carbon atoms to "*" of the partial structure (I) in the compound (A) can be formed by, for example, allowing a group represented by the following formula (a) (hereinafter, may be also referred to as "group (a)") to react with a primary amine compound represented by the following formula (b) (hereinafter, may be also referred to as "compound (b)") and a carbonyl compound represented by the following formula (c) (hereinafter, may be also referred to as "compound (c)") in a solvent such as propylene glycol monomethyl ether acetate, in a case of a group represented by the following formula (1') (hereinafter, may be also referred to as "group (1')"), wherein in the above formula (1), $R^2$ and $R^4$ are identical groups, and $R^3$ and $R^5$ are identical groups. In this case, bonds can be formed by an oxygen atom of —OH included in the group (a) and a carbon atom at the ortho-position of the aromatic ring to which —OH bonds with a nitrogen atom included in the compound (b) and carbon atoms included in two compounds (c), whereby the oxazine structure fused to an aromatic ring is formed.

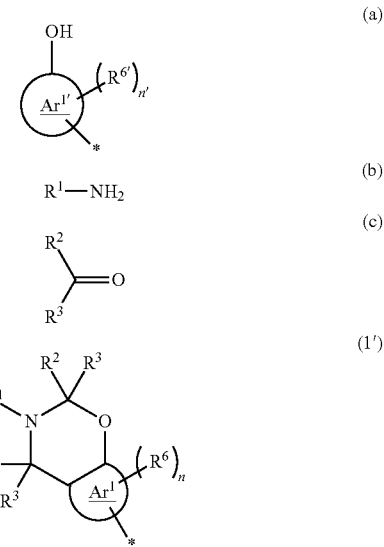

In the above formulae (a), (b), (c) and (1'), $R^1$ represents a monovalent organic group having 1 to 20 carbon atoms; $R^2$ and $R^3$ each independently represent a hydrogen atom or a monovalent organic group having 1 to 20 carbon atoms; $R^{6'}$ represents a hydroxy group, a halogen atom, a nitro group or a monovalent organic group having 1 to 20 carbon atoms; n' is an integer of 0 to 9, wherein in a case in which n' is no less than 2, a plurality of $R^{6'}$-s may be identical or different, or the plurality of $R^{6'}$-s may taken together represent a ring structure having 4 to 20 ring atoms together with the carbon chain to which the plurality of $R^{6'}$-s bond, and wherein in a case in which n' is no less than 2, a case in which two of the plurality of $R^{6'}$-s bond to carbon atoms at two ortho-positions of the aromatic ring to which —OH in the above formula (a) bonds is excluded; $Ar^{1'}$ represents a group obtained by removing (n'+2) or (n'+1) hydrogen atoms on the aromatic ring from the arene having 6 to 20 carbon atoms; $R^6$ represents a hydroxy group, a halogen atom, a nitro group or a monovalent organic group having 1 to 20 carbon atoms; n is an integer of 0 to 9, wherein in a case in which n is no less than 2, a plurality of $R^6$s may be identical or different, or the plurality of $R^6$ may taken together represent a ring structure having 4 to 20 ring atoms together with the carbon chain to which the plurality of $R^6$ bond; $Ar^1$ represents a group obtained by removing (n+3) or (n+2) hydrogen atoms on the aromatic ring from the arene having 6 to 20 carbon atoms; and * denotes a bonding site to a part other than the group (a) in the compound (a), or a part other than the group (1') in the compound (A).

Alternatively, a group (hereinafter, may be also referred to as "group (I-B)") provided by bonding of a hydrogen atom to "*" of the partial structure (I) in the compound (A) can be formed by, for example, allowing a group represented by the following formula (b') (hereinafter, may be also referred to as "group (b')") to react with a compound represented by the following formula (a') (hereinafter, may be also referred to as "compound (a')") and a carbonyl compound represented by the following formula (c') (hereinafter, may be also referred to as "compound (c')") in a solvent such as propylene glycol monomethyl ether acetate, in a case of a group represented by the following formula (1″) (hereinafter, may be also referred to as "group (1″)"), wherein in the above formula (1), $R^2$ and $R^4$ are identical groups, and $R^3$ and $R^5$ are identical groups. In this case, bonds can be formed by an oxygen atom of —OH included in the compound (a') and a carbon atom at the ortho-position of the aromatic ring to which —OH bonds with a nitrogen atom included in the compound (b') and carbon atoms included in two compounds (c'), whereby the oxazine structure fused to an aromatic ring is formed.

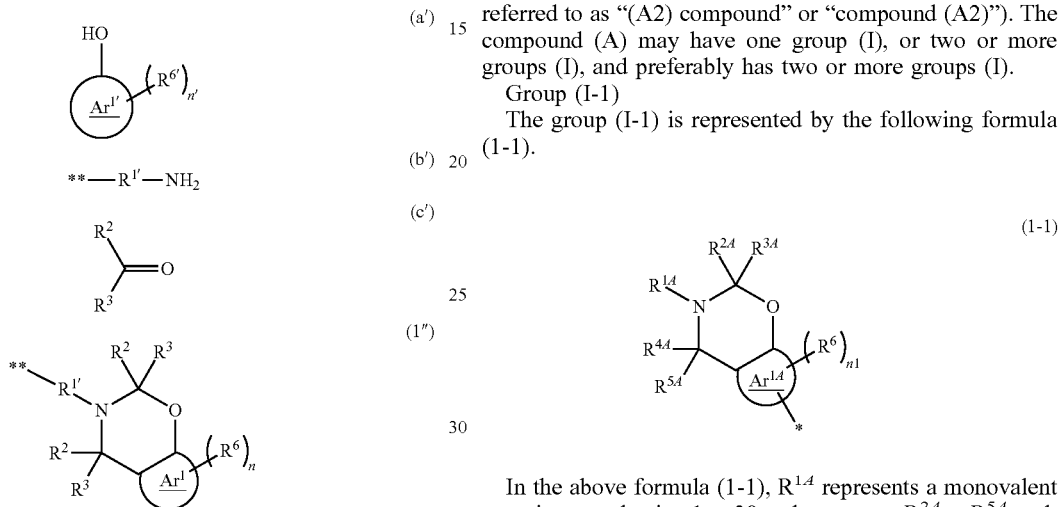

In the above formulae (a'), (b'), (c') and (1″), R″ represents a divalent organic group having 1 to 20 carbon atoms; $R^2$ and $R^3$ each independently represent a hydrogen atom or a monovalent organic group having 1 to 20 carbon atoms; $R^{6'}$ represents a hydroxy group, a halogen atom, a nitro group or a monovalent organic group having 1 to 20 carbon atoms; n' is an integer of 0 to 9, wherein in a case in which n' is no less than 2, a plurality of $R^{6'}$-s may be identical or different, or the plurality of $R^{6'}$-s may taken together represent a ring structure having 4 to 20 ring atoms together with the carbon chain to which the plurality of $R^{6'}$-s bond, and wherein in a case in which n' is no less than 2, a case in which two of a plurality of $R^{6'}$-s bond to carbon atoms at two ortho-positions of the aromatic ring to which —OH in the above formula (a') bonds is excluded; $Ar^{1'}$ represents a group obtained by removing (n'+1) hydrogen atoms on the aromatic ring from the arene having 6 to 20 carbon atoms; $R^6$ represents a hydroxy group, a halogen atom, a nitro group or a monovalent organic group having 1 to 20 carbon atoms; n is an integer of 0 to 9, wherein in a case in which n is no less than 2, a plurality of $R^6$s may be identical or different, or the plurality of $R^6$ may taken together represent a ring structure having 4 to 20 ring atoms together with the carbon chain to which the plurality of $R^6$ bond; $Ar^1$ represents a group obtained by removing (n+2) hydrogen atoms on the aromatic ring from the arene having 6 to 20 carbon atoms; and ** denotes a bonding site to a part other than the group (b') in the compound (b'), or a part other than the group (1″) in the compound (A).

Examples of the compound (c) and compound (c') include aldehydes such as formaldehyde, acetaldehyde, propionaldehyde and benzaldehyde, and the like. Of these, formaldehyde is preferred. Paraformaldehyde may be used in place of formaldehyde, and paraldehyde may be used in place of acetaldehyde.

The compound (A) is exemplified by a group represented by the following formula (1-1) (hereinafter, may be also referred to as "group (I-1)"), a group represented by the following formula (1-2) (hereinafter, may be also referred to as "group (I-2)") or a compound including a combination thereof, and the like (hereinafter, the group (I-1) and the group (I-2) may be taken together also referred to as "group (I)"; and the compound (A) having the group (I-1) may be also referred to as "(A1) compound" or "compound (A1)" and the compound (A) having the group (I-2) may be also referred to as "(A2) compound" or "compound (A2)"). The compound (A) may have one group (I), or two or more groups (I), and preferably has two or more groups (I).

Group (I-1)

The group (I-1) is represented by the following formula (1-1).

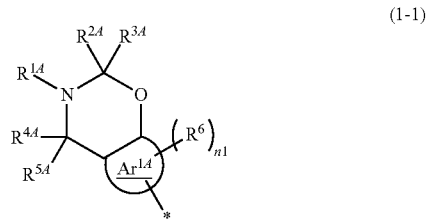

In the above formula (1-1), $R^{1A}$ represents a monovalent organic group having 1 to 20 carbon atoms; $R^{2A}$ to $R^{5A}$ each independently represent a hydrogen atom or a monovalent organic group having 1 to 20 carbon atoms; $Ar^{1A}$ represents a group obtained by removing (n1+3) or (n1+2) hydrogen atoms on the aromatic ring from the arene having 6 to 20 carbon atoms; $R^{6A}$ represents a hydroxy group, a halogen atom, a nitro group or a monovalent organic group having 1 to 20 carbon atoms; n1 is an integer of 0 to 9, wherein in a case in which n1 is no less than 2, a plurality of $R^{6A}$s may be identical or different, or two or more of the plurality of $R^{6A}$s may taken together represent a ring structure having 4 to 20 ring atoms together with the carbon chain to which the two or more of the plurality of $R^{6A}$s bond; and * denotes a bonding site to a part other than the group (I-1) in the compound (A).

Group (I-2)

The group (I-2) is represented by the following formula (1-2).

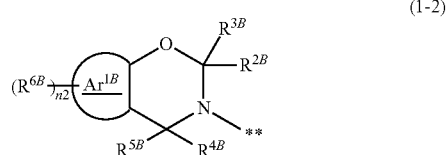

In the above formula (1-2), $R^{2B}$ to $R^{5B}$ each independently represent a hydrogen atom or a monovalent organic group having 1 to 20 carbon atoms; $Ar^{1B}$ represents a group obtained by removing (n2+2) hydrogen atoms on an aromatic ring from the arene having 6 to 20 carbon atoms; $R^{6B}$ represents a hydroxy group, a halogen atom, a nitro group or a monovalent organic group having 1 to 20 carbon atoms; n2 is an integer of 0 to 10, wherein in a case in which n2 is no less than 2, a plurality of $R^{6B}$s may be identical or different, or two or more of the plurality of $R^{6B}$s may taken together represent a ring structure having 4 to 20 ring atoms together with the carbon chain to which the two or more of the plurality of $R^{6B}$s bond; and ** denotes a bonding site to a part other than the group (I-2) in the compound (A).

Examples of the monovalent organic group having 1 to 20 carbon atoms represented by $R^{1A}$ include groups similar to those exemplified as the monovalent organic group having 1 to 20 carbon atoms which may be represented by $R^2$ to $R^6$ in the above formula (1), and the like.

$R^{1A}$ represents preferably a monovalent hydrocarbon group, a heteroaryl group or an arylamino group, more preferably a monovalent hydrocarbon group or a heteroaryl group, still more preferably a monovalent chain hydrocarbon group, a monovalent aromatic hydrocarbon group or a heteroaryl group that includes oxygen atom in the ring, particularly preferably an alkyl group, an alkoxyalkyl group, a cyanoalkyl group, an aryl group, a halogenatedaryl group, an aralkyl group, a halogenatedaralkyl group or a furyl group, and further particularly preferably a methyl group, an ethyl group, a propyl group, a butyl group, a methoxymethyl group, a methoxyethyl group, a methoxypropyl group, a methoxybutyl group, a cyano methyl group, a cyano ethyl group, a cyano propyl group, a cyano butyl group, a phenyl group, a naphthyl group, a benzyl group, a naphthylmethyl group, a monofluorophenyl group, a monofluoronaphthyl group, a monofluorobenzyl group, a monofluoronaphthylmethyl group, a difluorophenyl group, a difluoronaphthyl group, a difluorobenzyl group, a difluoronaphthylmethyl group or a furyl group.

Examples of the monovalent organic group having 1 to 20 carbon atoms which may be represented by $R^{2A}$ to $R^{5A}$ and $R^{2B}$ to $R^{5B}$ include groups similar to those exemplified as the monovalent organic group having 1 to 20 carbon atoms which may be represented by $R^2$ to $R^5$ in the above formula (1), and the like. Of these, a hydrogen atom and the alkyl group are preferred, and a hydrogen atom is more preferred.

Examples of $Ar^{1A}$ and $Ar^{1B}$ include groups similar to those exemplified as $Ar^1$ in the above formula (1), and the like. As the arene in $Ar^{1A}$ and $Ar^{1B}$, benzene and naphthalene are preferred.

As $R^{6A}$ and $R^{6B}$, a hydroxy group, a halogen atom and a monovalent organic group having 1 to 20 carbon atoms are preferred, a monovalent hydrocarbon group is more preferred, and an alkyl group is still more preferred.

As n1 and n2, 0 to 3 are preferred, 0 to 2 are more preferred, 0 and 1 are still more preferred, and 0 is particularly preferred.

The lower limit of the number of the group (I) included in the compound (A) is preferably 2, and more preferably 3. The upper limit of the number of the group (I) is preferably 6, and more preferably 5. When the number of the group (I) in the compound (A) falls within the above range, the degree of crosslinking in the film to be formed is increased, and consequently, the composition for resist underlayer film formation provides more improved flatness, and more improved solvent resistance and etching resistance of the film.

The compound (A) is exemplified by: a compound represented by the following formula (i-1) (hereinafter, may be also referred to as "compound (i-1)") as the compound (A1), a compound represented by the following formula (i-2) (hereinafter, may be also referred to as "compound (i-2)") as the compound (A2) (the compound (i-1) and the compound (i-2) may be taken together also referred to as "compound (i)"), and the like; a resin (hereinafter, may be also referred to as "resin (I)"); and the like. The compound (i-1), the compound (i-2) and the resin (I) are described below in this order.

Compound (i-1)

The compound (i-1) is represented by the following formula (i-1).

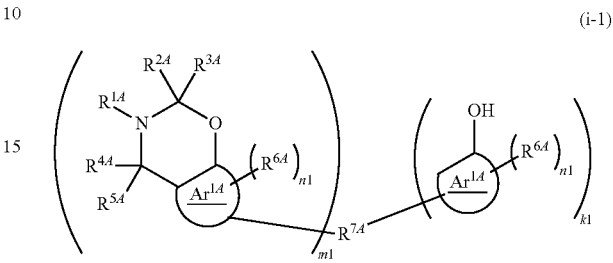

(i-1)

In the above formula (i-1), $R^{1A}$ to $R^{6A}$, $Ar^{1A}$ and n1 are as defined in the above formula (1-1); $R^{7A}$ represents an organic group having 1 to 30 carbon atoms and having a valency of (m1+k1); m1 is an integer of 1 to 10; k1 is an integer of 0 to 9; and (m1+k1) is no less than 2 and no greater than 10, wherein in a case in which m1 is no less than 2, a plurality of $R^{1A}$s may be identical or different, a plurality of $R^{2A}$s may be identical or different, a plurality of $R^{3A}$s may be identical or different, a plurality of $R^{4A}$s may be identical or different, a plurality of $R^{5A}$s may be identical or different, a plurality of $Ar^{1A}$s may be identical or different, and a plurality of n1s may be identical or different, and in a case there exist a plurality of $R^{6A}$s, the plurality of $R^{6A}$s may be identical or different, and two or more of the plurality of $R^{6A}$s may taken together represent a ring structure having 4 to 20 ring atoms together with the atom chain to which the two or more of the plurality of $R^{6A}$s bond, or one or more of $R^{6A}$s and $R^{7A}$ may taken together represent a ring structure having 4 to 20 ring atoms together with the carbon chain to which the one or more of $R^{6A}$s and $R^{7A}$ bond.

Compound (i-2)

The compound (i-2) is represented by the following formula (i-2).

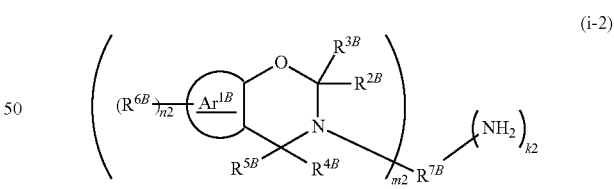

(i-2)

In the above formula (i-2), $R^{2B}$ to $R^{6B}$, $Ar^{1B}$ and n2 are as defined in the formula (1-2); $R^{7B}$ represents an organic group having 1 to 30 carbon atoms and having a valency of (m2+k2); m2 is an integer of 1 to 10; k2 is an integer of 0 to 9; and (m2+k2) is no less than 2 and no greater than 10, wherein in a case in which m2 is no less than 2, a plurality of $R^{2B}$s may be identical or different, a plurality of $R^{3B}$s may be identical or different, a plurality of $R^{4B}$s may be identical or different, a plurality of $R^{5B}$s may be identical or different, a plurality of $Ar^{1B}$s may be identical or different, and a plurality of n2s may be identical or different, and in a case in which there exist a plurality of $R^{6B}$s, the plurality of $R^{6B}$s may be identical or different, or two or more of the plurality of $R^{6B}$s may taken together represent a ring structure having 4 to 20 ring atoms together with the atom chain to which the two or more of the plurality of $R^{6B}$s bond.

Examples of the ring structure having 6 to 20 ring atoms which may be taken together represented by the two or more of the a plurality of $R^{6A}$s together with the atom chain to which the two or more of the a plurality of $R^{6A}$s bond, and the ring structure having 6 to 20 ring atoms which may be taken together represented by the two or more of the a plurality of $R^{6B}$s together with the atom chain to which the two or more of the a plurality of $R^{6B}$s bond include: alicyclic structures such as a cyclohexane structure and a cyclohexene structure; aliphatic heterocyclic structures such as an azacyclohexane structure and an azacyclohexene structure; aromatic heterocyclic structures such as a pyridine structure; and the like.

The lower limit of m1 and m2 is preferably 2, and more preferably 3. The upper limit of m is preferably 8, and more preferably 6.

The lower limit of k1 and k2 is preferably 6 and more preferably 4, and k is preferably 0 or 1 and more preferably 0.

The lower limit of (m1+k1) and (m2+k2) is preferably 2, and more preferably 3. The upper limit of (m1+k1) and (m2+k2) is preferably 8, and more preferably 6.

The organic group represented by $R^{7A}$ is exemplified by: a hydrocarbon group having 1 to 30 carbon atoms; a group (α) that includes a divalent hetero atom-containing group between two adjacent carbon atoms of the hydrocarbon group having 1 to 30 carbon atoms; or a group (β) obtained from the hydrocarbon group having 1 to 30 carbon atoms or the group (α) that includes the divalent hetero atom-containing group by substituting a part or all of hydrogen atoms comprised therein with a monovalent hetero atom-containing group, and exemplary organic group represented by $R^{7A}$ includes groups obtained by removing (m1+k1-1) hydrogen atoms from the group exemplified as the monovalent organic group having 1 to 20 carbon atoms which may be represented by $R^2$ to $R^6$.

$R^{7A}$ represents preferably: a group derived from methane; an aliphatic hydrocarbon group having 2 to 20 carbon atoms; a group derived from an arene or a heteroarene; a group (γ) having an aromatic ring and a benzyl-positioned carbon atom bonded to this aromatic ring with a hydrogen atom bonded to the carbon atom having been removed; or a group derived from a lactone compound.

Examples of the monovalent hetero atom-containing group which may be included in $R^{7A}$ include a hydroxy group, a sulfanyl group, a halogen atom, a nitro group, a cyano group, and the like.

Examples of the aliphatic hydrocarbon group having 2 to 20 carbon atoms include those having 2 to 20 carbon atoms among the chain hydrocarbon groups and the alicyclic hydrocarbon groups exemplified above as $R^{1A}$, and the like.

When $R^{7A}$ represents the aliphatic hydrocarbon group having 2 to 20 carbon atoms or the group derived from a lactone compound, a degree of molecular freedom of the compound (A1) is believed to be more increased, thereby enabling the flatness of the resist underlayer film formed from the composition for resist underlayer film formation to be more improved.

More specific examples of $R^{7A}$ include groups represented by the following formulae (2-1-1) to (2-1-8) (hereinafter, may be also referred to as "groups (2-1-1) to (2-1-8)"), and the like.

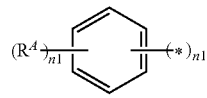
(2-1-1)

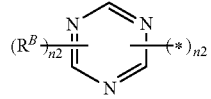
(2-1-2)

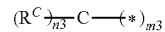
(2-1-3)

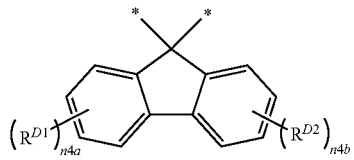
(2-1-4)

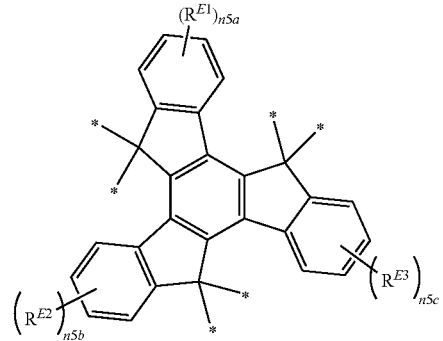
(2-1-5)

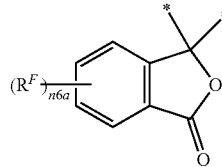
(2-1-6)

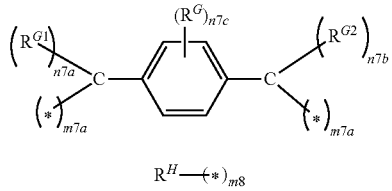
(2-1-7)

(2-1-8)

In the above formulae (2-1-1) to (2-1-8), * denotes a binding site to the carbon atom on the aromatic ring in $Ar^{1A}$ of the above formula (i-1).

In the above formula (2-1-1), $R^A$ represents a hydroxy group, a halogen atom, a nitro group or a monovalent organic group having 1 to 20 carbon atoms; n1 is an integer of 0 to 4, wherein in a case in which n1 is no less than 2, a plurality of $R^A$s may be identical or different; m1 is an integer of 2 to 6; and (n1+m1) is no greater than 6. It is preferred that n1 is 0 or 1, and more preferably 0. It is preferred that m1 is 2, 3, 4 or 6, and more preferably 3.

In the above formula (2-1-2), $R^B$ represents a hydroxy group, a halogen atom, a nitro group or a monovalent organic group having 1 to 20 carbon atoms; n2 is 0 or 1; and m2 is 2 or 3, wherein (n2+m2) is no greater than 3. It is preferred that n2 is 0, m2 is 3. and n3 is 2 or 3.

In the above formula (2-1-3), $R^C$ represents a hydrogen atom, a hydroxy group, a halogen atom, a nitro group or a monovalent organic group having 1 to 20 carbon atoms; n3 is an integer of 0 to 2, wherein in a case in which n3 is 2, a plurality of $R^C$s may be identical or different; m3 is an integer of 2 to 4; and (n3+m3) is 4. It is preferred that n3 is 2 or 3.

In the above formula (2-1-4), $R^{D1}$ and $R^{D2}$ each independently represent a hydroxy group, a halogen atom, a nitro group or a monovalent organic group having 1 to 20 carbon atoms; n4a and n4b are each independently an integer of 0 to 4, wherein in a case in which n4a is no less than 2, a plurality of $R^{D1}$s may be identical or different, and in a case in which n4b is no less than 2, a plurality of $R^{D2}$s may be identical or different. It is preferred that n4a and n4b are each 0 or 1, and more preferably 0.

In the above formula (2-1-5), $R^{E1}$ to $R^{E3}$ each independently represent a hydroxy group, a halogen atom, a nitro group or a monovalent organic group having 1 to 20 carbon atoms; and n5a, n5b and n5c are each independently an integer of 0 to 4, wherein in a case in which n5a is no less than 2, a plurality of $R^{E1}$s may be identical or different, in a case in which n5b is no less than 2, a plurality of $R^{E2}$s may be identical or different, and in a case in which n5c is no less than 2, a plurality of $R^{E3}$s may be identical or different. It is preferred that n5a, n5b and n5c are each 0 or 1, and more preferably 0.

In the above formula (2-1-6), $R^F$ represents a hydroxy group, a halogen atom, a nitro group or a monovalent organic group having 1 to 20 carbon atoms; n6a is an integer of 0 to 4, wherein in a case in which n6a is no less than 2, a plurality of $R^F$s may be identical or different. It is preferred that n6a is 0 or 1, and more preferably 0.

In the above formula (2-1-7), $R^{G1}$ and $R^{G2}$ each independently represent a hydroxy group, a halogen atom, a nitro group or a monovalent organic group having 1 to 20 carbon atoms; n7a and n7b are each independently an integer of 0 to 2, wherein in a case in which n7a is 2, two $R^{G1}$s may be identical or different, and in a case in which n7b is 2, two $R^{G2}$s may be identical or different; $R^{G3}$ represents a hydroxy group, a halogen atom, a nitro group or a monovalent organic group having 1 to 20 carbon atoms; n7c is an integer of 0 to 4, wherein in a case in which n7c is no less than 2, a plurality of $R^{G3}$s may be identical or different; m7a and m7b are each independently an integer of 1 to 3; (n7a+m7a) is 3; and (n7b+m7b) is 3. It is preferred that n7c is 0 or 1, and more preferably 0.

In the above formula (2-1-8), $R^H$ represents an aliphatic hydrocarbon group having 2 to 20 carbon atoms and having a valency of m8, wherein m8 is preferably an integer of 1 to 4, and more preferably 3 or 4.

$R^{7A}$ represents preferably any of the groups (2-1-1) to (2-1-8), and more preferably the group (2-1-6) or the group (2-1-8).

Examples of the compound (i-1) include compounds represented by the following formulae (i-1-1) to (i-1-14) (hereinafter, may be also referred to as "compounds (i-1-1) to (i-1-14)"), and the like.

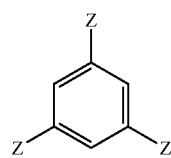

(i-1-1)

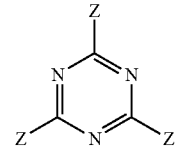

(i-1-2)

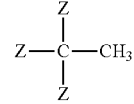

(i-1-3)

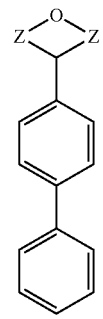

(i-1-4)

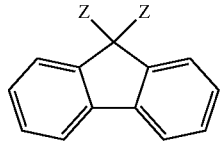

(i-1-5)

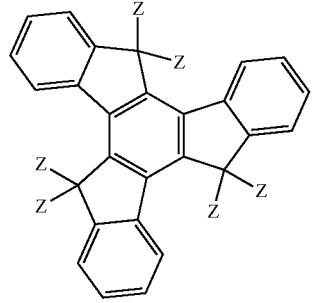

(i-1-6)

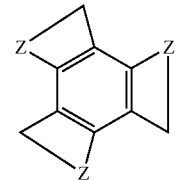

(i-1-7)

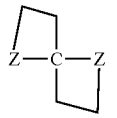

(i-1-8)

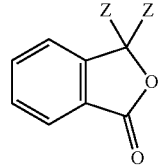

(i-1-9)

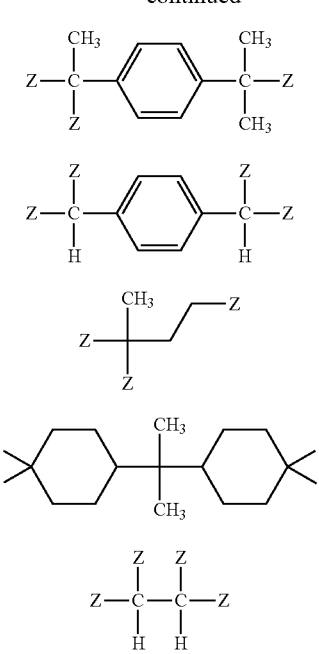

In the above formulae (i-1-1) to (i-1-14), Zs each independently represent the group (I-1).

The compound (i-1) is preferably any of the compounds (i-1-1) to (i-1-14), and more preferably any of the compounds (i-1-9) and (i-1-12) to (i-1-14).

Examples of the organic group represented by $R^{7B}$ in the above formula (i-2) include: a hydrocarbon group; a group (α) that includes a divalent hetero atom-containing group between two adjacent carbon atoms of the hydrocarbon group; a group (β) obtained from the group (α) that includes the hydrocarbon group or the divalent hetero atom-containing group by substituting a part or all of hydrogen atoms included therein with a monovalent hetero atom-containing group, as well as a group obtained from the group exemplified as the monovalent organic group having 1 to 20 carbon atoms which may be represented by $R^2$ to $R^6$ by removing (m2+k2-1) hydrogen atoms, and the like.

$R^{7B}$ represents preferably: a group derived from methane; an aliphatic hydrocarbon group having 2 to 20 carbon atoms; an aliphatic heterocyclic group; a group derived from an arene or a heteroarene; a group derived from a trialkylamine; a group (γ) having an aromatic ring and a benzyl-positioned carbon atom bonded to this aromatic ring with a hydrogen atom bonded to the carbon atom having been removed; or a group (δ) including a plurality of arenediyl groups bonded to the linking group.

Examples of the linking group in the group (δ) include a hydrocarbon group, —O—, —S—, —SO$_2$—, and the like. Examples of the aliphatic hydrocarbon group having 2 to 20 carbon atoms, and substituent of the group in $R^{7B}$ include groups similar to those exemplified for $R^{7B}$ described above, and the like.

When $R^{7B}$ represents the group derived from methane, the aliphatic hydrocarbon group having 2 to 20 carbon atoms, the group derived from an arene or a heteroarene or the group (δ), a degree of molecular freedom of the compound (A2) is believed to be more increased, thereby enabling the flatness of the resist underlayer film formed from the composition for resist underlayer film formation to be more improved. Examples of the monovalent hetero atom-containing group which may be included in $R^{7B}$ include a hydroxy group, a sulfanyl group, a halogen atom, a nitro group, a cyano group, and the like.

More specific examples of $R^{7B}$ include groups represented by the following formulae (2-2-1) to (2-2-11) (hereinafter, may be also referred to as "groups (2-2-1) to (2-2-11)"), and the like.

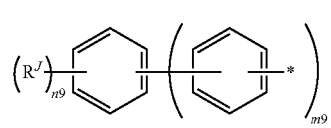

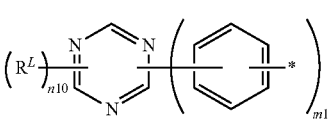

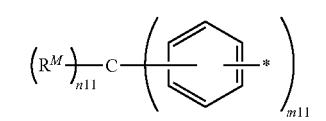

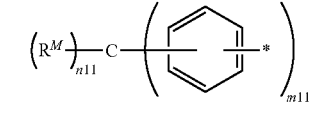

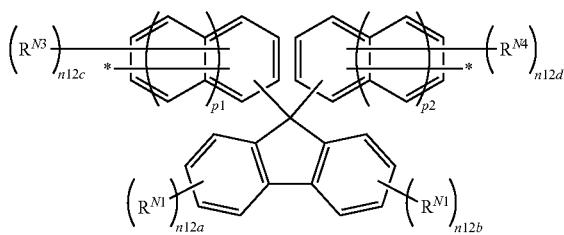

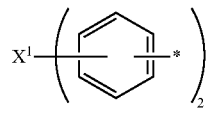

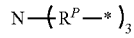

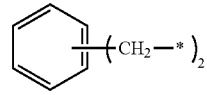

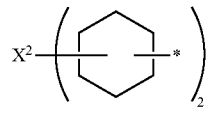

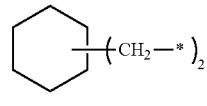

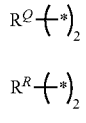

In the above formulae (2-2-1) to (2-2-11), * denotes a binding site to the nitrogen atom in the above formula (i-2).

In the above formula (2-2-1), $R^J$ represents a hydroxy group, a halogen atom, a nitro group or a monovalent organic group having 1 to 20 carbon atoms; n9 is an integer of 0 to 4, wherein in a case in which n9 is no less than 2, a plurality of $R^J$s may be identical or different; m9 is an integer of 2 to 6; and (n9+m9) is no greater than 6.

In the above formula (2-2-2), $R^L$ represents a hydroxy group, a halogen atom, a nitro group or a monovalent organic group having 1 to 20 carbon atoms; n10 is 0 or 1; m10 is 2 or 3; and (n10+m10) is no greater than 3.

In the above formula (2-2-3), $R^M$ represents a hydrogen atom, a hydroxy group, a halogen atom, a nitro group or a monovalent organic group having 1 to 20 carbon atoms; n11 is an integer of 0 to 2, wherein in a case in which n11 is 2, a plurality of $R^M$s may be identical or different; m11 is an integer of 2 to 4; and (n11+m11) is 4.

In the above formula (2-2-4), $R^{N1}$ and $R^{N2}$ each independently represent a hydroxy group, a halogen atom, a nitro group or a monovalent organic group having 1 to 20 carbon atoms; n12a and n12b are each independently an integer of 0 to 4, wherein in a case in which n12a is no less than 2, a plurality of $R^{N1}$B may be identical or different, and in a case in which n12b is no less than 2, a plurality of $R^{N2}$s may be identical or different; p1 and p2 are each independently an integer of 0 to 4; $R^{N3}$ and $R^{N4}$ each independently represent a monovalent organic group having 1 to 20 carbon atoms; n12c and n12d are each independently an integer of 0 to 9, wherein in a case in which n12c is no less than 2, a plurality of $R^{N3}$s may be identical or different, and in a case in which n12d is no less than 2, a plurality of $R^{N4}$s may be identical or different.

In the above formula (2-2-5), $X^1$ represents —O—, —S—, —SO$_2$— or an alkanediyl group having 1 to 10 carbon atoms.

In the above formula (2-2-6), $R^P$s each independently represent an alkanediyl group having 1 to 5 carbon atoms.

In the above formula (2-2-8), $X^2$ represents —O—, —S—, —SO$_2$— or an alkanediyl group having 1 to 10 carbon atoms.

In the above formula (2-2-10), $R^Q$ represents a divalent aliphatic hydrocarbon group or a divalent aliphatic heterocyclic group.

In the above formula (2-2-11), $R^R$ represents an arenediyl group.

As $R^{7B}$, groups (2-2-1) to (2-2-11) are preferred, and groups (2-1-1) to (2-1-5) are more preferred.

In a case in which the compound (A2) has a naphthalene ring, i.e., in a case in which the arene in $Ar^{1B}$ in the above formula (i-2) is naphthalene and/or $R^{6B}$ in the above formula (i-2) has a naphthalene ring, or the resin (I) described later is the compound (A2) having a structural unit that includes a naphthalene ring, the resist film formed from the composition for resist underlayer film formation enables both a refractive index and an extinction coefficient to fall within ranges suitable for formation of a resist pattern from a resist composition, respectively.

It is also preferred that in the compound (A), two or more oxazine structures are fused to a single aromatic ring. Examples of such a compound include a compound represented by the following formula (i-3), and the like.

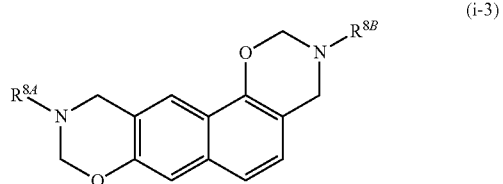
(i-3)

In the above formula (i-3), $R^{8A}$ and $R^{8B}$ each independently represent a monovalent organic group having 1 to 20 carbon atoms.

The lower limit of the molecular weight of the compound (i) is preferably 300, more preferably 400, still more preferably 500, and particularly preferably 600. The upper limit of the molecular weight is preferably 3,000, more preferably 2,000, and still more preferably 1,500. When the molecular weight of the compound (i) falls within the above range, a more improvement of the flatness of the resist underlayer film is enabled.

Resin (I)

The resin (I) has the group (I). The resin (I) is exemplified by a resin having an aromatic ring in the main chain thereof, a resin not having an aromatic ring in the main chain thereof but having the aromatic ring in the side chain thereof, and the like. The term "main chain" as referred to means the longest one of the chains constituted of atoms in the compound (A). The term "side chain" as referred to means a chain constituted of atoms in the compound (A) other than the longest one. The resin (I) is typically a compound including a plurality of the groups (I).

The resin (I) is exemplified by: a resin obtained by allowing a resin having the group (a) to react with the compound (b) and the compound (c) at the group (a) to introduce the group (I-A); a resin obtained by allowing a resin having a structure of the compound (b') to react with the compound (a') and the compound (c') at the amino group to introduce the group (I-B); and the like.

The resin (I) is exemplified by a phenol resin, a naphthol resin, a fluorene resin, an aromatic ring-containing vinyl-based resin, an acenaphthylene resin, an indene resin, an arylene resin, a triazine resin, a pyrene resin, a fullerene resin, a calixarene resin, and the like, according to classification by the type of a basic resin.

Phenol Resin

The phenol resin is a resin having a structural unit derived from a phenol compound, the structural unit including the group (I). The phenol resin may be synthesized by, for example, allowing the phenol compound to react with an aldehyde compound by using an acidic catalyst or an alkaline catalyst to form the group (I-1) from a phenol structure of a resulting resin.

Examples of the phenol compound include phenol, cresol, xylenol, resorcinol, bisphenol A, p-tert-butylphenol, p-octylphenol, and the like.

Examples of the aldehyde compound include:
aldehydes such as formaldehyde; aldehyde sources such as paraformaldehyde and trioxane; and the like.

Naphthol Resin

The naphthol resin is a resin having a structural unit derived from a naphthol compound, the structural unit including the group (I). The naphthol resin may be synthesized by, for example, allowing the naphthol compound to react with an aldehyde compound by using an acidic catalyst or an alkaline catalyst to form the group (I-1) from a naphthol structure of a resulting resin.

Examples of the naphthol compound include α-naphthol, β-naphthol, 1,5-dihydroxynaphthalene, 2,7-dihydroxynaphthalene, and the like.

Fluorene Resin

The fluorene resin is a resin having a structural unit derived from a fluorene compound, the structural unit including the group (I). The fluorene resin may be synthesized by, for example, allowing the phenol compound having a hydroxyaryl structure to react with an aldehyde compound by using an acidic catalyst or an alkaline catalyst to form the group (I-1) from the hydroxyaryl structure of a resulting resin. Alternatively, the fluorene resin may be synthesized by forming the group (I-2) from an amino group-containing structure of a resin derived from a fluorene compound including an amino group.

Examples of the fluorene compound include 9,9-bis(4-hydroxyphenyl)fluorene, 9,9-bis(4-hydroxyphenyl)fluorene, 9,9-bis(6-hydroxynaphthyl)fluorene, and the like.

Aromatic Ring-Containing Vinyl-Based Resin

The aromatic ring-containing vinyl-based resin is a resin having a structural unit derived from a compound having an aromatic ring and a polymerizable carbon-carbon double bond, the structural unit including the group (I). The aromatic ring-containing vinyl-based resin may be synthesized by, for example, forming the group (I-1) from a phenol structure of a resin having a structural unit derived from a compound having: an aromatic ring including a phenolic hydroxyl group; and a polymerizable carbon-carbon double bond. Alternatively, the aromatic ring-containing vinyl-based resin may be synthesized by forming the group (I-2) from an amino group-containing structure of a resin having a structural unit derived from a compound having: an aromatic ring including an amino group; and a polymerizable carbon-carbon double bond.

Acenaphthylene Resin

The acenaphthylene resin is a resin having a structural unit derived from an acenaphthylene compound, the structural unit including the group (I). The acenaphthylene resin may be synthesized by, for example, forming the group (I-1) from a phenol structure of a resin having a structural unit derived from an acenaphthylene compound having a hydroxyaryl structure. Alternatively, the acenaphthylene resin may be synthesized by forming the group (I-2) from an amino group-containing structure of a resin having a structural unit derived from an acenaphthylene compound having the amino group-containing structure.

Indene Resin

The indene resin is a resin having a structural unit derived from an indene compound, the structural unit including the group (I). The indene resin may be synthesized by, for example, forming the group (I-1) from a hydroxyaryl structure of a resin having a structural unit derived from an indene compound having a hydroxyaryl structure. Alternatively, the indene resin may be synthesized by forming the group (I-2) from an amino group-containing structure of a resin having a structural unit derived from an indene compound having the amino group-containing structure.

Arylene Resin

The arylene resin is a resin having an arylene skeleton including the group (I). The arylene resin may be synthesized by, for example, forming the group (I-1) from a phenol structure of a resin having an arylene skeleton having a hydroxyaryl structure. Alternatively, the arylene resin may be synthesized by forming the group (I-2) from an amino group-containing structure of a resin having an arylene skeleton having an amino group-containing structure. Examples of the arylene skeleton include a phenylene skeleton, a naphthylene skeleton, a biphenylene skeleton, and the like.

Triazine Resin

The triazine resin is a resin having a triazine skeleton including the group (I). The triazine resin may be synthesized by, for example, forming the group (I-1) from a phenol structure of a resin having a triazine skeleton having a hydroxyaryl structure. Alternatively, the triazine resin may be synthesized by forming the group (I-2) from an amino group-containing structure of a resin having a triazine skeleton having an amino group-containing structure.

Pyrene Resin

The pyrene resin is a resin having a pyrene skeleton including the group (I). The pyrene resin may be synthesized by, for example, forming the group (I-1) from a phenol structure of a resin having a pyrene skeleton having a hydroxyaryl structure. Alternatively, the pyrene resin may be synthesized by forming the group (I-2) from an amino group-containing structure of a resin having a pyrene skeleton having an amino group-containing structure. The resin having a pyrene skeleton having a hydroxyaryl structure is obtained by, for example, allowing a pyrene compound including a phenolic hydroxyl group to react with an aldehyde compound by using an acidic catalyst. The resin having a pyrene skeleton having an amino group-containing structure is obtained by, for example, allowing a pyrene compound having an amino group-containing structure to react with an aldehyde compound by using an acidic catalyst.

Fullerene Resin

The fullerene resin is a resin having a fullerene skeleton including the group (I). The fullerene resin may be synthesized by, for example, forming the group (I-1) from a phenol structure of a resin having a fullerene skeleton having a hydroxyaryl structure. Alternatively, the fullerene resin may be synthesized by forming the group (I-2) from an amino group-containing structure of a resin having a fullerene skeleton having an amino group-containing structure.

In the case in which the compound (A) is the phenol resin, the naphthol resin, the fluorene resin, the aromatic ring-containing vinyl-based resin, the acenaphthylene resin, the indene resin, the arylene resin, the triazine resin, the pyrene resin or the fullerene resin, the lower limit of a weight average molecular weight (Mw) of the compound (A) is preferably 500 and more preferably 1,000. Meanwhile, the upper limit of Mw is preferably 50,000, more preferably 10,000, and still more preferably 8,000.

The lower limit of a ratio (Mw/Mn) of Mw to a number average molecular weight (Mn) of the compound (A) is typically 1, and preferably 1.1. The upper limit of Mw/Mn is preferably 5, more preferably 3, and still more preferably 2.

When Mw and Mw/Mn of the compound (A) fall within the above range, more improvements of the flatness and surface coating characteristics which may be provided by the composition for resist underlayer film formation are enabled.

The Mw and the Mn of the compound (A) are determined by gel permeation chromatography using GPC columns ("G2000 HXL"×2, and "G3000 HXL"×1) available from Tosoh Corporation, a differential refractometer as a detector and mono-dispersed polystyrene as a standard under analytical conditions involving a flow rate of 1.0 mL/min, an elution solvent of tetrahydrofuran and a column temperature of 40° C.

Calixarene Resin

The calixarene resin is a cyclic oligomer including the group (I) in which a plurality of aromatic rings, each having a phenolic hydroxyl group bonded thereto, circularly bond to each other via hydrocarbon groups. The calixarene resin including the group (I) can be synthesized by, for example, forming the group (I-1) from a phenol structure of a calixarene resin.

In the case in which the compound (A) is the calixarene resin, the lower limit of a molecular weight of the calixarene resin is preferably 500, more preferably 700, and still more preferably 1,000 in light of more improvement of the flatness which may be provided by the composition for resist underlayer film formation. The upper limit of the molecular weight is preferably 5,000, more preferably 3,000, and still more preferably 1,500.

The lower limit of the content of the compound (A) with respect to the total solid content in the composition for resist underlayer film formation is preferably 70% by mass, more preferably 80% by mass, and still more preferably 85% by mass. Meanwhile, the upper limit of the content is, for example, 100% by mass. The "total solid content" as referred to means the sum of the components other than the solvent (B) in the composition for resist underlayer film formation.

The lower limit of the content of the compound (A) in the composition for resist underlayer film formation is preferably 1% by mass, more preferably 3% by mass, and still more preferably 5% by mass. The upper limit of the content is preferably 50% by mass, more preferably 30% by mass, and still more preferably 15% by mass.

(B) Solvent

The solvent (B) is not particularly limited as long as it can dissolve or disperse the compound (A), and the optional component contained as needed.

The solvent (B) is exemplified by an alcohol solvent, a ketone solvent, an ether solvent, an ester solvent, a nitrogen-containing solvent, and the like. The solvent (B) may be used either alone of one type, or in combination of two or more types thereof.

Examples of the alcohol solvent include: monoalcohol solvents such as methanol, ethanol and n-propanol; polyhydric alcohol solvents such as ethylene glycol and 1,2-propylene glycol; and the like.

Examples of the ketone solvent include: chain ketone solvents such as methyl ethyl ketone and methyl-iso-butylketone; cyclic ketone solvents such as cyclohexanone; and the like.

Examples of the ether solvent include: polyhydric alcohol ether solvents, e.g., chain ether solvents such as n-butyl ether, and cyclic ether solvents such as tetrahydrofuran; polyhydric alcohol partial ether solvents such as diethylene glycol monomethyl ether; and the like.

Examples of the ester solvent include: carbonate solvents such as diethyl carbonate; mono ester acetate solvents such as methyl acetate and ethyl acetate; lactone solvents such as γ-butyrolactone; polyhydric alcohol partial ether carboxylate solvents such as diethylene glycol monomethyl ether acetate and propylene glycol monomethyl ether acetate; ester lactate solvents such as methyl lactate and ethyl lactate; and the like.

Examples of the nitrogen-containing solvent include: chain nitrogen-containing solvents such as N,N-dimethylacetamide, cyclic nitrogen-containing solvents such as N-methylpyrrolidone; and the like.

Of these, the ether solvent and the ester solvent are preferred, and an ether solvent and an ester solvent each having a glycol structure are more preferred in light of superior film formability.

Exemplary ether solvent and exemplary ester solvent each having a glycol structure include propylene glycol monomethyl ether, propylene glycol monoethyl ether, propylene glycol monopropyl ether, propylene glycol monomethyl ether acetate, propylene glycol monoethyl ether acetate, propylene glycol monopropyl ether acetate, and the like. Of these, propylene glycol monomethyl ether acetate is particularly preferred.

The lower limit of the percentage content of the ether solvent and the ester solvent, each having a glycol structure, in the solvent (B) is preferably 20% by mass, more preferably 60% by mass, still more preferably 90% by mass, and particularly preferably 100% by mass.

(C) Acid Generating Agent

The acid generating agent (C) generates an acid by an action of heat and/or light to promote the crosslinking of molecules of the compound (A). When the composition for resist underlayer film formation contains the acid generating agent (C), the crosslinking reaction of molecules of the compound (A) is promoted and consequently the hardness of the formed film is enabled to be further increased. The acid generating agent (C) may be used either alone of one type, or in combination of two or more types thereof.

The acid generating agent (C) is exemplified by an onium salt compound, an N-sulfonyloxyimide compound, and the like.

The onium salt compound is exemplified by a sulfonium salt, a tetrahydrothiophenium salt, an iodonium salt, an ammonium salt, and the like.

Examples of the sulfonium salt include triphenylsulfonium trifluoromethanesulfonate, triphenylsulfonium nonafluoro-n-butanesulfonate, triphenylsulfonium 2-bicyclo[2.2.1]hept-2-yl-1,1,2,2-tetrafluoroethanesulfonate, 4-cyclohexylphenyldiphenylsulfonium trifluoromethanesulfonate, and the like.

Examples of the tetrahydrothiophenium salt include 1-(4-n-butoxynaphthalen-1-yl)tetrahydrothiophenium trifluoromethanesulfonate, 1-(4-n-butoxynaphthalen-1-yl)tetrahydrothiophenium nonafluoro-n-butanesulfonate, and the like.

Examples of the iodonium salt include diphenyliodonium trifluoromethanesulfonate, diphenyliodonium nonafluoro-n-butanesulfonate, diphenyliodonium 2-bicyclo[2.2.1]hept-2-yl-1,1,2,2-tetrafluoroethanesulfonate, bis(4-t-butylphenyl)iodonium trifluoromethanesulfonate, bis(4-t-butylphenyl)iodonium nonafluoro-n-butanesulfonate, and the like.

Examples of the ammonium salt include triethylammonium trifluoromethanesulfonate, triethylammonium nonafluoro-n-butanesulfonate, and the like.

Examples of the N-sulfonyloxyimide compound include N-(trifluoromethanesulfonyloxy)bicyclo[2.2.1]hept-5-ene-2,3-dicarboxyimide, N-(nonafluoro-n-butanesulfonyloxy)bicyclo[2.2.1]hept-5-ene-2,3-dicarboxyimide, and the like.

Of these, the acid generating agent (C) is preferably the onium salt compound, more preferably the iodonium salt or the ammonium salt, still more preferably the iodonium salt, and particularly preferably bis(4-t-butylphenyl)iodonium nonafluoro-n-butanesulfonate.

In the case in which the composition for resist underlayer film formation contains the acid generating agent (C), the lower limit of the content of the acid generating agent (C) with respect to 100 parts by mass of the compound (A) is preferably 0.1 parts by mass, more preferably 1 part by mass, and still more preferably 3 parts by mass. The upper limit of the content is preferably 20 parts by mass, more preferably 15 parts by mass, and still more preferably 12 parts by mass. When the content of the acid generating agent (C) falls within the above range, the crosslinking reaction of molecules of the compound (A) may be facilitated more effectively.

The crosslinking agent (D) forms crosslinking bonds between components such as the compound (A) in the composition for resist underlayer film formation, or forms cross-linked structures by molecules of itself, through an action of heat and/or an acid. When the composition for resist underlayer film formation contains the crosslinking agent (D), an increase in the hardness of the formed resist underlayer film is enabled. The crosslinking agent (D) may be used either alone of one type, or in combination of two or more types thereof.

Examples of the crosslinking agent (D) include: polyfunctional (meth)acrylate compounds such as trimethylolpropane tri(meth)acrylate, ditrimethylolpropane tetra(meth)acrylate and pentaerythritol tri(meth)acrylate; epoxy compounds such as a novolak epoxy resin, a bisphenol epoxy resin, an alicyclic epoxy resin and an aliphatic epoxy resin; hydroxymethyl group-substituted phenol compounds such as 2-hydroxymethyl-4,6-dimethylphenol, 1,3,5-trihydroxymethylbenzene and 3,5-dihydroxymethyl-4-methoxytoluene[2,6-bis(hydroxymethyl)-p-cresol]; alkoxyalkyl group-containing phenol compounds such as a methoxymethyl group-containing phenol compound and an ethoxymethyl group-containing phenol compound; compounds having an alkoxyalkylated amino group; random copolymers of an acenaphthylene with hydroxymethylacenaphthylene which is represented by the following formula (11-P); compounds represented by the following formulae (11-1) to (11-12); and the like.

(11-P)

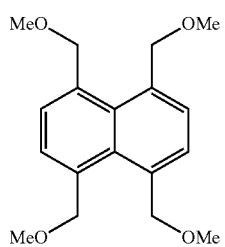

(11-1)

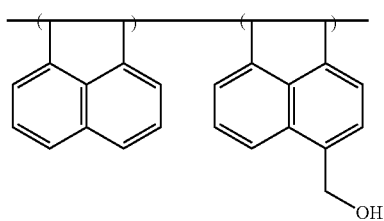

(11-2)

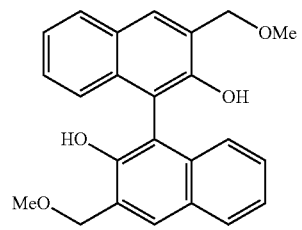

(11-3)

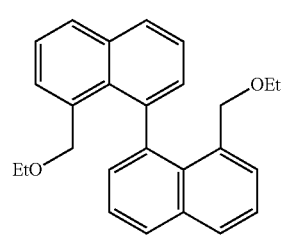

(11-4)

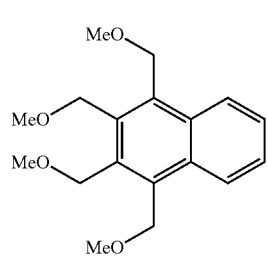

(11-5)

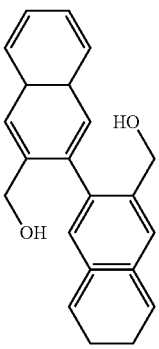

(11-6)

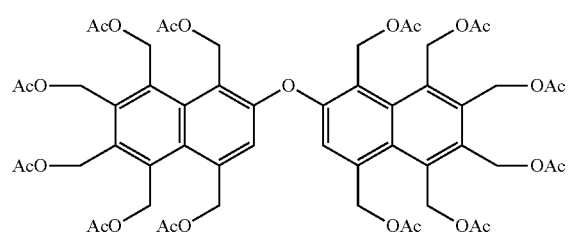

(11-7)

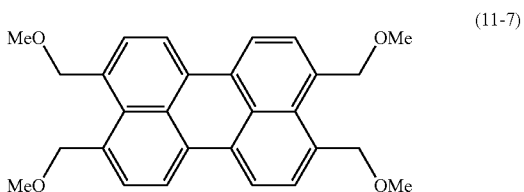

(11-8)

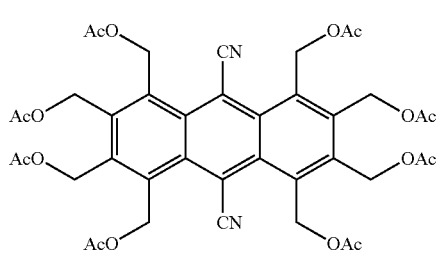

(11-9)

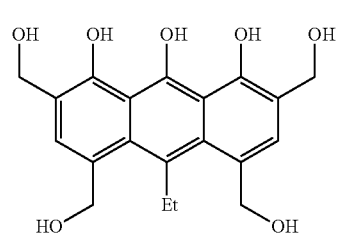

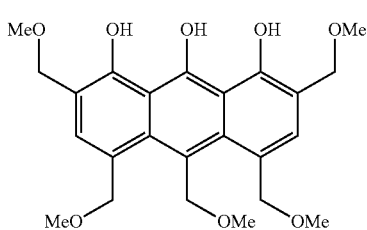
(11-10)

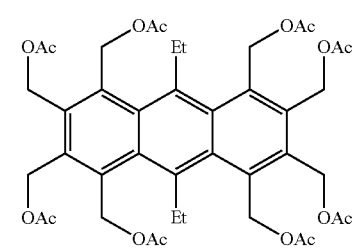
(11-11)

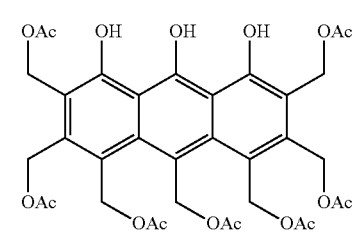
(11-12)

In the above formulae, Me represents a methyl group; Et represents an ethyl group; and Ac represents an acetyl group.

The methoxymethyl group-containing phenol compound is exemplified by a compound represented by the following formula (11-Q).

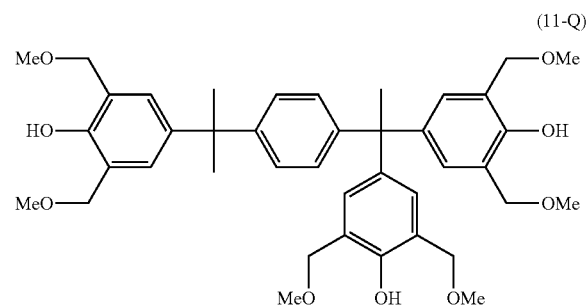 [SMILES: COCc1cc(C(C)(C)c2ccc(C(C)(c3cc(COC)c(O)c(COC)c3)c3cc(COC)c(O)c(COC)c3)cc2)cc(COC)c1O]
(11-Q)

Examples of the compound having an alkoxyalkylated amino group include nitrogen-containing compounds having a plurality of active methylol groups in a molecule thereof, wherein the hydrogen atom of the hydroxyl group of at least one of the methylol groups is substituted with an alkyl group such as a methyl group or a butyl group, and the like; examples thereof include (poly)methylolated melamines, (poly)methylolated glycolurils, (poly)methylolated benzoguanamines, (poly)methylolated ureas, and the like. It is to be noted that a mixture constituted with a plurality of substituted compounds described above may be used as the compounds having an alkoxyalkylated amino group, and the compound having an alkoxyalkylated amino group may contain an oligomer component formed through partial self-condensation thereof. An exemplary compound having an alkoxyalkylated amino group may include 1,3,4,6-tetrakis(methoxymethyl)glycoluril.

Among these crosslinking agents (D), the methoxymethyl group-containing phenol compound, the compound having an alkoxyalkylated amino group, and the random copolymer of acenaphthylene with hydroxymethylacenaphthylene are preferred, the methoxymethyl group-containing phenol compound and the compound having an alkoxyalkylated amino group are more preferred, and 4,4'-(1-(4-(1-(4-hydroxy-3,5-bis(methoxymethyl)phenyl)-1-methylethyl)phenyl)ethylidene)bis(2,6-bis(methoxymethyl)phenol (the compound represented by the above formula (11-Q)) and 1,3,4,6-tetra(methoxymethyl)glycoluril are still more preferred.

In the case in which the composition for resist underlayer film formation contains the crosslinking agent (D), the lower limit of the content of the crosslinking agent (D) with respect to 100 parts by mass of the compound (A) is preferably 0.1 parts by mass, more preferably 0.5 parts by mass, still more preferably 1 part by mass, and particularly preferably 3 parts by mass. The upper limit of the content is preferably 100 parts by mass, more preferably 50 parts by mass, still more preferably 30 parts by mass, and particularly preferably 20 parts by mass. When the content of the crosslinking agent (D) falls within the above range, the crosslinking reaction of molecules of the compound (A) may be allowed to occur more effectively.

Other Optional Component

Other optional component is exemplified by a surfactant, an adhesion aid, and the like.

Surfactant

When the composition for resist underlayer film formation contains the surfactant, coating characteristics thereof can be improved, and consequently uniformity of the surface of the formed film may be improved and occurrence of the unevenness of coating can be inhibited. The surfactant may be used either alone of one type, or in combination of two or more types thereof.

Examples of the surfactant include nonionic surfactants such as polyoxyethylene lauryl ether, polyoxyethylene stearyl ether, polyoxyethylene oleyl ether, polyoxyethylene n-octylphenyl ether, polyoxyethylene n-nonylphenyl ether, polyethylene glycol dilaurate and polyethylene glycol distearate, and the like. Furthermore, examples of commercially available surfactant include KP341 (available from Shin-Etsu Chemical Co., Ltd.); Polyflow No. 75 and Polyflow No. 95 (each available from Kyoeisha Chemical Co., Ltd.); EFTOP EF101, EFTOP EF204, EFTOP EF303 and EFTOP EF352 (each available from Tochem Products Co. Ltd.); Megaface F171, Megaface F172 and Megaface F173 (each available from DIC Corporation); Fluorad FC430, Fluorad FC431, Fluorad FC135 and Fluorad FC93 (each available from Sumitomo 3M Limited); ASAHI GUARD AG710, Surflon S382, Surflon SC101, Surflon SC102, Surflon SC103, Surflon SC104, Surflon SC105 and Surflon SC106 (each available from Asahi Glass Co., Ltd.); and the like.

In the case in which the composition for resist underlayer film formation contains the surfactant, the lower limit of the content of the surfactant with respect to 100 parts by mass of the compound (A) is preferably 0.01 parts by mass, more preferably 0.05 parts by mass, and still more preferably 0.1 parts by mass. The upper limit of the content is preferably 10 parts by mass, more preferably 5 parts by mass, and still more preferably 1 part by mass. When the content of the surfactant falls within the above range, the coating characteristics of the composition for resist underlayer film formation is enabled to be more improved.

Preparation Procedure of Composition for Resist Underlayer Film Formation

The composition for resist underlayer film formation may be prepared, for example, by mixing the compound (A) and the solvent (B), as well as the acid generating agent (C) and the other optional component as needed, at a certain ratio, preferably followed by filtering a mixture thus obtained through a membrane filter, etc. having a pore size of about 0.1 μm. The lower limit of the solid content concentration of the composition for resist underlayer film formation is preferably 0.1% by mass, more preferably 1% by mass, still more preferably 3% by mass, and particularly preferably 5% by mass. The upper limit of the solid content concentration of the composition for resist underlayer film formation is preferably 50% by mass, more preferably 30% by mass, still more preferably 20% by mass, and particularly preferably 15% by mass.

The composition for resist underlayer film formation is capable of providing a film having superior flatness and being superior in solvent resistance and etching resistance, and can therefore be suitably used for formation of a resist underlayer film in production of a semiconductor device and the like. In addition, the composition for film formation can also be used for formation of a protective film, an insulating film, a colored cured film in a display device and the like.

Resist Underlayer Film

The resist underlayer film according to another embodiment of the present invention is formed from the composition for resist underlayer film formation according to the embodiment of the present invention. Since the resist underlayer film is formed from the composition for resist underlayer film formation described above, the resist underlayer film has superior flatness, and is superior in both solvent resistance and etching resistance.

Method for Resist Underlayer Film Formation

The method for resist underlayer film formation according to yet another embodiment includes: applying the aforementioned composition for resist underlayer film formation directly or indirectly on a substrate (hereinafter, may be also referred to as "applying step"); and heating a coating film obtained by the applying of the composition (hereinafter, may be also referred to as "heating step"). According to the method for resist underlayer film formation, formation of a resist underlayer film having superior flatness, and being superior in both solvent resistance and etching resistance is enabled since the aforementioned composition for resist underlayer film formation is used.

Applying Step

In this step, the composition for resist underlayer film formation of the embodiment of the invention is applied directly or indirectly on the substrate.

Examples of the substrate include a silicon wafer, a wafer coated with aluminum, and the like. The applying procedure of the composition for resist underlayer film formation is not particularly limited, and for example, an appropriate procedure such as spin coating, cast coating and roll coating may be employed to form a coating film.

Heating Step
Heating Step

In this step, the coating film obtained by the applying step is heated. The resist underlayer film is thus formed.

Heating of the coating film is typically carried out in an ambient air. The lower limit of a heating temperature is preferably 120° C., more preferably 150° C., and still more preferably 200° C. The upper limit of the heating temperature is preferably 500° C., more preferably 400° C., and still more preferably 300° C. When the heating temperature is less than 120° C., oxidative crosslinking may not sufficiently proceed, and characteristics necessary for use in the resist underlayer film may not be exhibited. The lower limit of the heating time period is preferably 15 sec, more preferably 30 sec, and still more preferably 45 sec. The upper limit of the heating time period is preferably 1,200 sec, more preferably 600 sec, and still more preferably 300 sec.

The coating film may be preheated at a temperature of no less than 60° C. and no greater than 100° C. before being heated at a temperature of no less than 120° C. and no greater than 500° C. The lower limit of the heating time period in the preheating is preferably 10 sec, and more preferably 30 sec. The upper limit of the heating time period is preferably 300 sec, and more preferably 180 sec.

It is to be noted that in the method for resist underlayer film formation, the resist underlayer film is formed through the heating of the coating film; however, in a case in which the composition for resist underlayer film formation contains the acid generating agent (C) and the acid generating agent (C) is a radiation-sensitive acid generating agent, the resist underlayer film may be formed also by hardening the film through a combination of an exposure and heating. The radioactive ray used for the exposure may be appropriately selected from: electromagnetic waves such as visible rays, ultraviolet rays, far ultraviolet rays, X-rays and γ radiations; particle rays such as electron beams, molecular beams and ion beams, and the like in accordance with the type of the acid generating agent (C).

The lower limit of the average thickness of the resist underlayer film formed is preferably 30 nm, more preferably 50 nm, and still more preferably 100 nm. The upper limit of the average thickness of the resist underlayer film formed is preferably 3,000 nm, more preferably 2,000 nm, and still more preferably 500 nm.

Production Method of Patterned Substrate

The production method of a patterned substrate according to still another embodiment includes: forming a resist pattern directly or indirectly on a resist underlayer film obtained by the aforementioned method for resist underlayer film formation (hereinafter, may be also referred to as "resist pattern-forming step"); and carrying out etching with the resist pattern used as a mask (hereinafter, may be also referred to as "etching step").

According to the production method of a patterned substrate, use of the resist underlayer film having superior in flatness and being superior in both solvent resistance and etching resistance obtained by the resist underlayer film-forming method enables a patterned substrate having a superior pattern configuration to be obtained.

Before the resist pattern-forming step, the production method of a patterned substrate may include as needed, a step of forming an intermediate layer (intermediate film) directly or indirectly on the resist underlayer film. Hereinafter, each step is explained.

Intermediate Layer-Forming Step

In this step, an intermediate layer is formed directly or indirectly on the resist underlayer film. The intermediate layer as referred to means a layer having a function that is exhibited or not exhibited by the resist underlayer film and/or the resist film in resist pattern formation in order to further enhance the function exhibited by the resist underlayer film and/or the resist film, or to impart to the resist underlayer film and/or the resist film a function not exhibited thereby. For example, when an antireflective film is provided as the intermediate layer, an antireflecting function of the resist underlayer film may be further enhanced.

The intermediate layer may be formed from an organic compound and/or an inorganic oxide. Examples of the organic compound include commercially available products such as: "DUV-42", "DUV-44", "ARC-28" and "ARC-29" (each available from Brewer Science); "AR-3" and "AR-19" (each available from Lohm and Haas Company); and the like. Exemplary inorganic oxide may include a composition for silicon-containing film formation. Examples of the inorganic oxide include commercially available products such as "NFC SOG01", "NFC SOG04" and "NFC SOG080" (each available from JSR Corporation), and the like. As the inorganic oxide, polysiloxanes, titanium oxides, aluminum oxides, tungsten oxides, and the like that are provided through a CVD process may also be used.

The forming procedure of the intermediate layer is not particularly limited, and for example, a coating procedure, a CVD technique, or the like may be employed. Of these, the coating procedure is preferred. In a case in which the coating procedure is employed, the intermediate layer may be successively provided after the resist underlayer film is formed. Moreover, the average thickness of the intermediate layer is appropriately selected in accordance with the function required for the intermediate layer, and the lower limit of the average thickness of the intermediate layer is preferably 10 nm, and more preferably 20 nm. The upper limit of the average thickness of the intermediate layer is preferably 3,000 nm, and more preferably 300 nm.

Resist Pattern-Forming Step

In this step, a resist pattern is formed directly or indirectly on the resist underlayer film. In the case in which the intermediate layer-forming step is carried out, a resist pattern is formed directly or indirectly on the intermediate layer. This step may be carried out by, for example, using a resist composition.

When the resist composition is used, specifically, the resist film is formed by applying the resist composition such that a resultant resist film has a predetermined thickness and thereafter subjecting the resist composition to prebaking to evaporate the solvent in the coating film.

Examples of the resist composition include a chemically amplified positive or negative resist composition that contains a radiation-sensitive acid generating agent; a positive resist composition containing an alkali-soluble resin and a quinone diazide-based photosensitizing agent; a negative resist containing an alkali-soluble resin and a crosslinking agent; and the like.

The lower limit of the solid content concentration of the resist composition is preferably 0.3% by mass, and more preferably 1% by mass. The upper limit of the solid content concentration of the resist composition is preferably 50% by mass, and more preferably 30% by mass. Moreover, the resist composition is generally used for forming a resist film, for example, after being filtered through a filter with a pore size of 0.2 μm. It is to be noted that a commercially available resist composition may be used as is in this step.

The applying procedure of the resist composition is not particularly limited, and examples thereof include a spin-coating method, and the like. The temperature of the prebaking may be appropriately adjusted in accordance with the type of the resist composition employed and the like; however, the lower limit of the temperature is preferably 30° C., and more preferably 50° C. The upper limit of the aforementioned temperature is preferably 200° C., and more preferably 150° C. The lower limit of a time period for the prebaking is preferably 10 sec, and more preferably 30 sec. The upper limit of the time period for the prebaking is preferably 600 sec, and more preferably 300 sec.

Next, the resist film formed is exposed by selective irradiation with a radioactive ray. The radioactive ray used in the exposure may be appropriately selected from: electromagnetic waves such as visible rays, ultraviolet rays, far ultraviolet rays, X-rays and γ radiations; particle rays such as electron beams, molecular beams and ion beams in accordance with the type of the radiation-sensitive acid generating agent used in the resist composition. Among these, far ultraviolet rays are preferred, and a KrF excimer laser beam (248 nm), and an ArF excimer laser beam (193 nm), an $F_2$ excimer laser beam (wavelength: 157 nm), a $Kr_2$ excimer laser beam (wavelength: 147 nm), an ArKr excimer laser beam (wavelength: 134 nm) and extreme ultraviolet rays (EUV; wavelength: 13.5 nm, etc.) are more preferred, and a KrF excimer laser beam, an ArF excimer laser beam and EUV are still more preferred.

Post-baking may be carried out after the exposure for the purpose of improving a resolution, a pattern profile, developability, and the like. The temperature of the post-baking may be appropriately adjusted in accordance with the type of the resist composition employed and the like; however, the lower limit of the temperature is preferably 50° C., and more preferably 70° C. The upper limit of the aforementioned temperature is preferably 200° C., and more preferably 150° C. The lower limit of a time period for the post-baking is preferably 10 sec, and more preferably 30 sec. The upper limit of the time period for the post-baking is preferably 600 sec, and more preferably 300 sec.

Next, the resist film exposed is developed with a developer solution to form a resist pattern. The development may be either a development with an alkali or a development with an organic solvent. In the case of the development with an alkali, examples of the developer solution include an alkaline aqueous solution that contains sodium hydroxide, potassium hydroxide, sodium carbonate, sodium silicate, sodium metasilicate, ammonia, ethylamine, n-propylamine, diethylamine, di-n-propylamine, triethylamine, methyldiethylamine, dimethylethanolamine, triethanolamine, tetramethylammonium hydroxide, tetraethylammonium hydroxide, pyrrole, piperidine, choline, 1,8-diazabicyclo[5.4.0]-7-undecene, 1,5-diazabicyclo[4.3.0]-5-nonene, or the like. An appropriate amount of a water soluble organic solvent, e.g., an alcohol such as methanol and ethanol, a surfactant, and the like may be added to the alkaline aqueous solution. Alternatively, in the case of the development with an organic solvent, examples of the developer solution include a variety of organic solvents exemplified as the solvent (B) in relation to the composition for resist underlayer film formation described above, and the like.

A predetermined resist pattern is formed by the development with the developer solution, followed by washing and drying.

In carrying out the resist pattern-forming step, without using the resist composition described above, other process may be employed, for example, a nanoimprint method may be adopted, or a directed self-assembling composition may be used.

Etching Step

In this step, etching is carried out with the aforementioned resist pattern as a mask to form a pattern on a substrate. The etching may be carried out once or multiple times. In other words, the etching may be carried out sequentially with patterns obtained by the etching as masks. However, in light of obtaining a pattern with a favorable shape, the etching is preferably carried out multiple times. When the etching is carried out multiple times, in a case in which the intermediate layer is not provided, the resist underlayer film and the substrate are subjected to etching sequentially in this order, whereas in a case in which the intermediate layer is provided, the intermediate layer, the resist underlayer film and the substrate are subjected to etching sequentially in this order. The etching step may be exemplified by dry etching, wet etching, and the like. Of these, in light of achieving a pattern with a more favorable shape, dry etching is preferred. For example, gas plasma such as oxygen plasma and the like may be used as the dry etching. After the dry etching, the substrate having a predetermined pattern can be obtained.

EXAMPLES

Hereinafter, the embodiment of the present invention will be explained in more detail by way of Examples, but the present invention is not in any way limited to these Examples. Measuring methods for various types of physical properties are shown below.

Weight Average Molecular Weight (Mw)

In the case in which the compound (A) is a polymer, the Mw of the compound (A) was determined by gel permeation chromatography using GPC columns ("G2000 HXL"×2, and "G3000 HXL"×1) available from Tosoh Corporation, a differential refractometer as a detector and mono-dispersed polystyrene as a standard under analytical conditions involving a flow rate of 1.0 mL/min, an elution solvent of tetrahydrofuran and a column temperature of 40° C.

Average Thickness of Film

The average thickness of the film was determined using a spectroscopic ellipsometer ("M2000D" available from J. A. WOOLLAM Co.).

Synthesis of Compound (A)

Synthesis of Compound (A1)

Compounds represented by the following formulae (A1-1) to (A1-18) were synthesized by the following procedure.

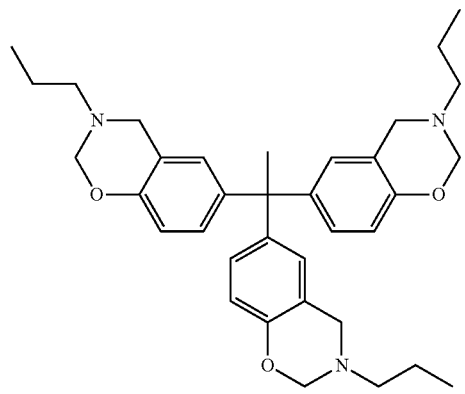

(A1-1)

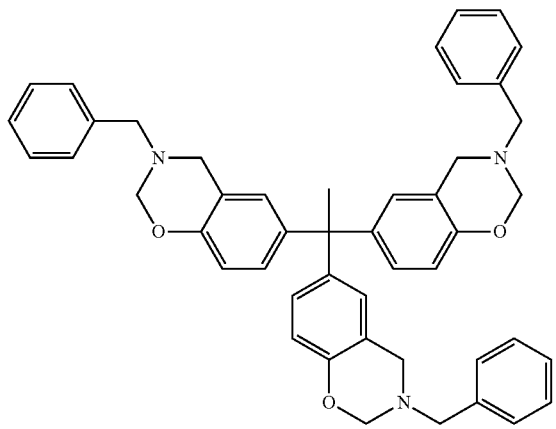

(A1-2)

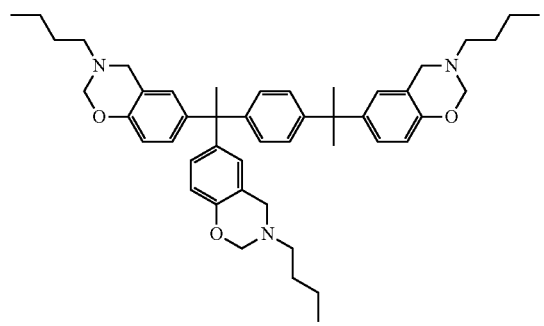

(A1-3)

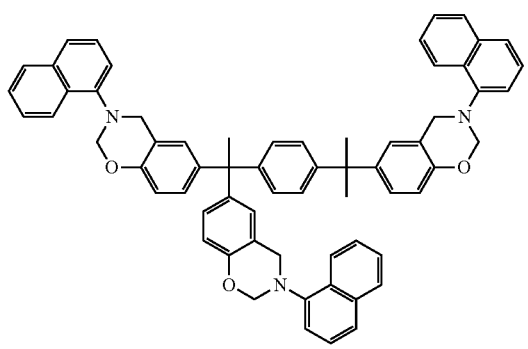

(A1-4)

(A1-5)
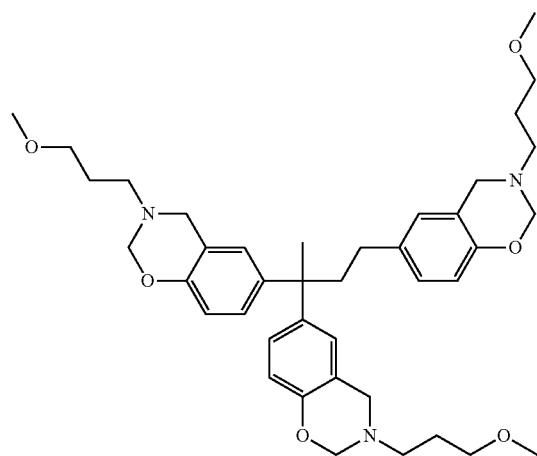
(A1-6)
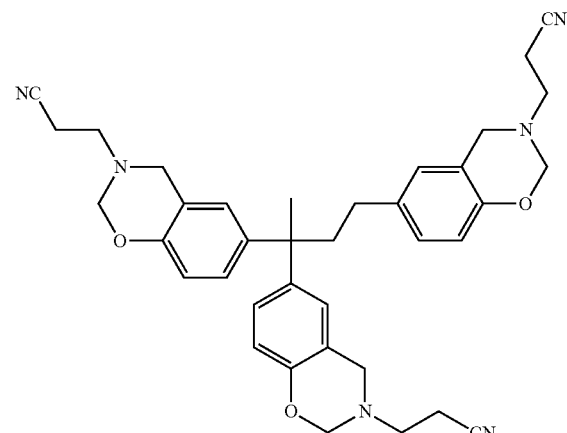
(A1-7)
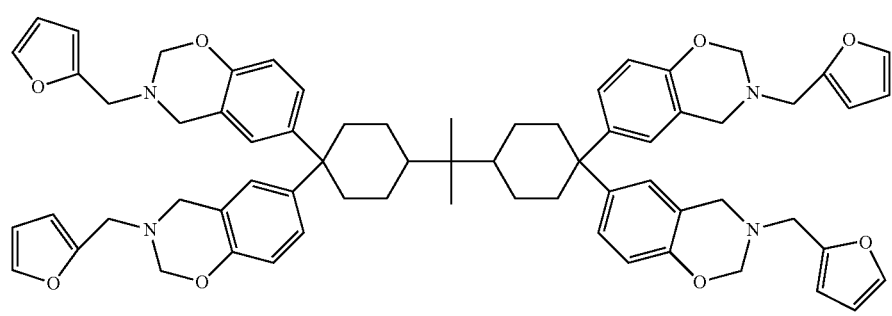
(A1-8)
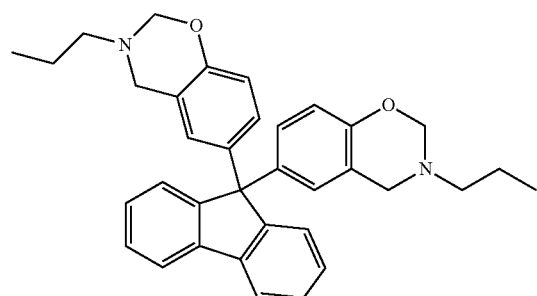
(A1-9)
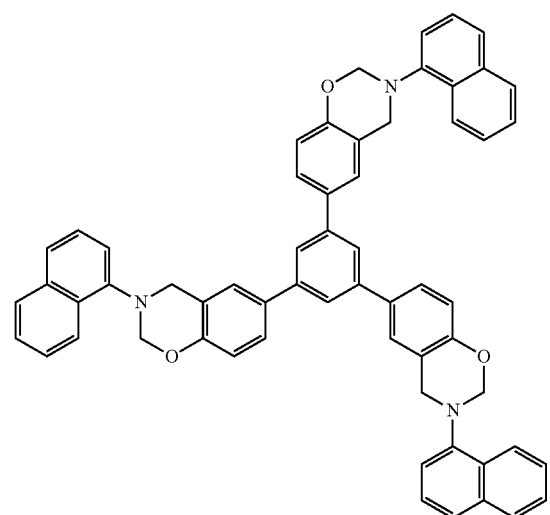

-continued
(A1-10)
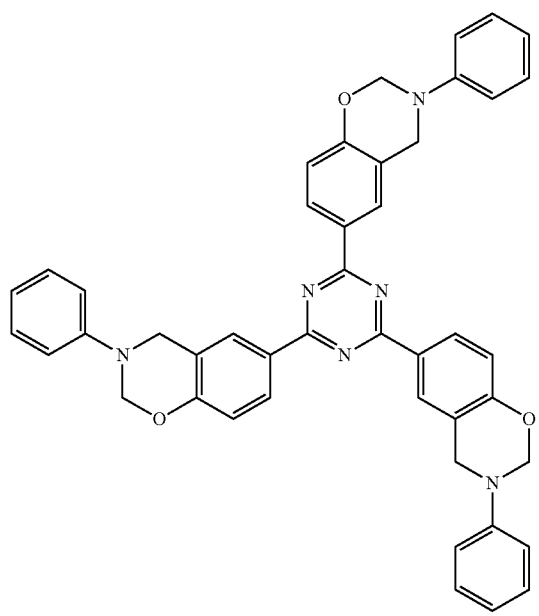
(A1-11)
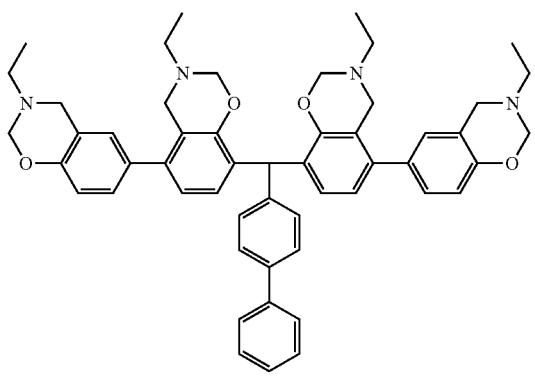
(A1-12)
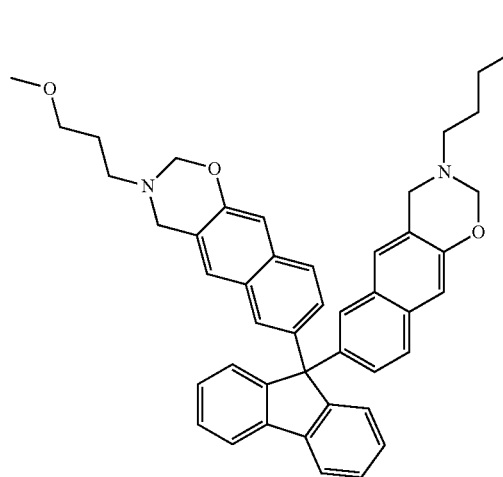
(A1-13)
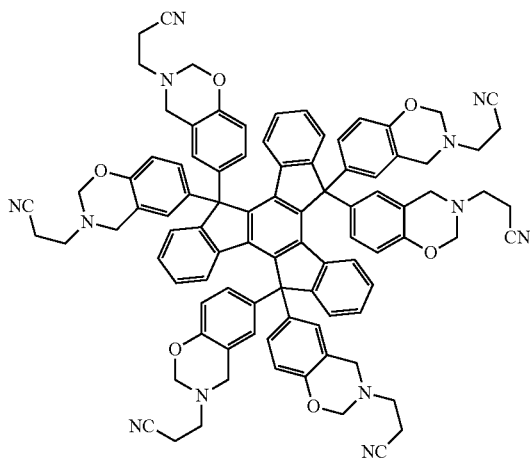
(A1-14)
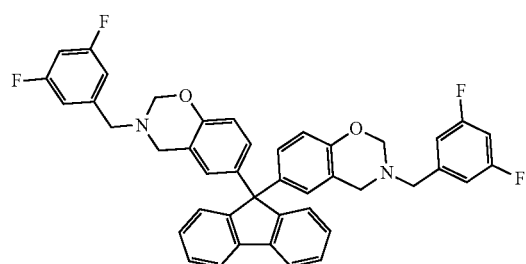
(A1-15)
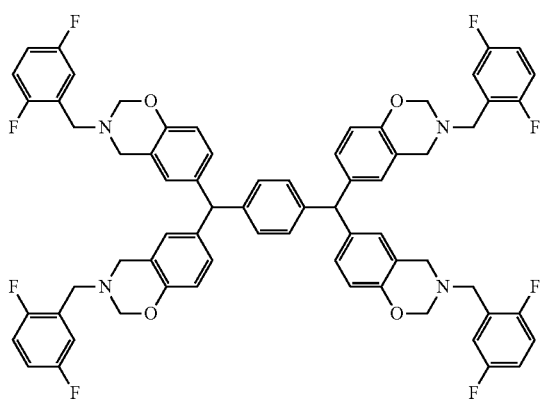

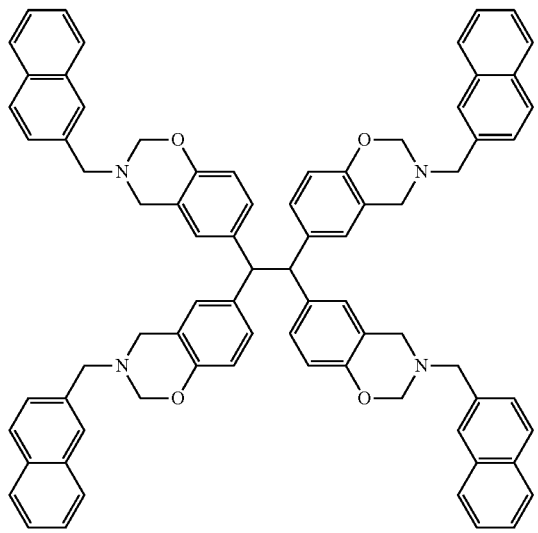

(A1-16)

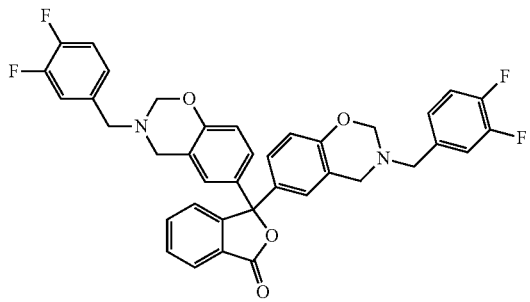

(A1-17)

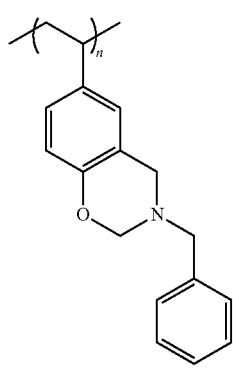

(A1-18)

Synthesis Example 1-1-1

Into a 500-mL three-neck flask equipped with a thermometer, a condenser and a magnetic stirrer were charged 15.0 g of 1,1,1-tris(4-hydroxyphenyl)ethane, 13.5 g of paraformaldehyde, 11.8 g of n-propylamine and 100 g of propylene glycol monomethyl ether acetate in a nitrogen atmosphere, and dissolution was permitted. The solution thus obtained was heated to 105° C. to allow for a reaction for 15 hrs. Methyl isobutyl ketone and water were added to the reaction solution, and extraction by liquid separation was conducted. Thereafter, the organic layer thus obtained was concentrated by using an evaporator, and then reprecipitation was carried out by charging the concentrate into hexane. The precipitate was recovered and then dried to give the compound represented by the above formula (A1-1).

Synthesis Examples 1-1-2 to 1-1-17

The compounds (A1-2) to (A1-17) were synthesized in a similar manner to Synthesis Example 1-1-1 through appropriately selecting the precursors.

Synthesis Example 1-1-18

Into a 500-mL three-neck flask equipped with a thermometer, a condenser and a magnetic stirrer were charged 15.0 g of polyhydroxystyrene (Maruzen Petrochemical Co., Ltd., "MARUKA LYNCUR M", Mw: 2,000), 12.3 g of paraformaldehyde, 19.7 g of benzylamine and 100 g of propylene glycol monomethyl ether acetate in a nitrogen atmosphere, and dissolution was permitted at room temperature. The solution thus obtained was heated to 105° C. to allow for a reaction for 15 hrs. Methyl isobutyl ketone and water were added to the reaction solution, and extraction by liquid separation was conducted. Thereafter, the organic layer thus obtained was concentrated by using an evaporator, and then reprecipitation was carried out by charging the concentrate into hexane. The precipitate was recovered and then dried to give the resin represented by the above formula (A1-18).

The resulting resin (A1-18) had the Mw of 4,100.

Synthesis of Compound (A2)

Compounds represented by the following formula (A2-1) to (A2-20) were synthesized according to a procedure show below.

(A2-1)
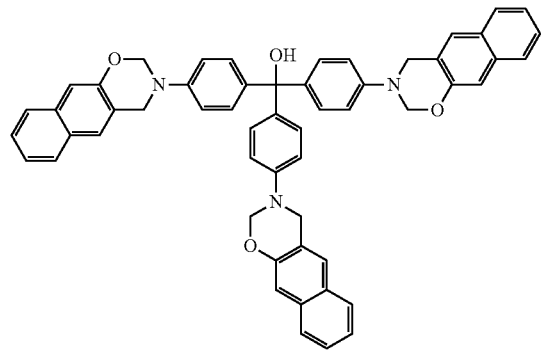
(A2-2)
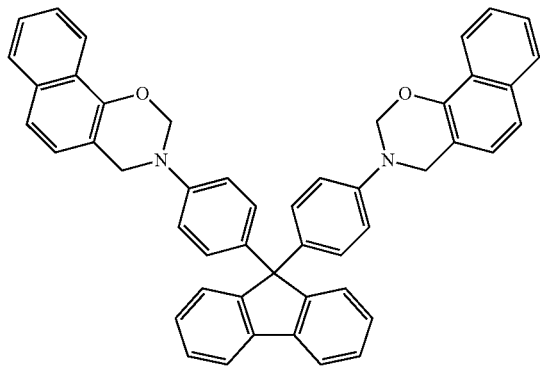
(A2-3)
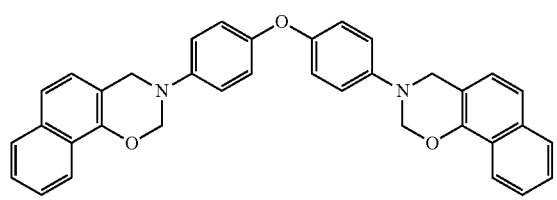
(A2-4)
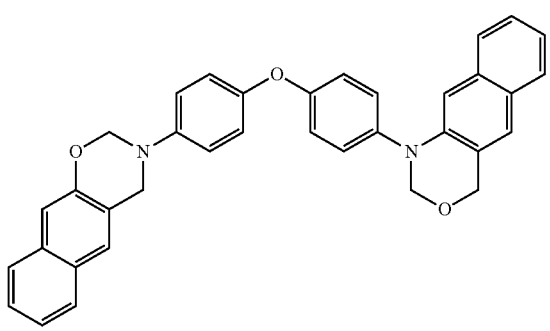
(A2-5)
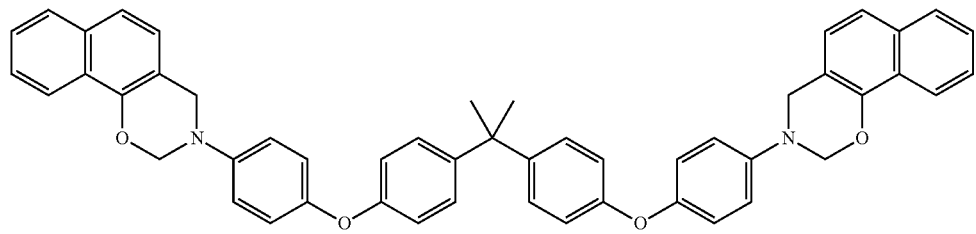
(A2-6)
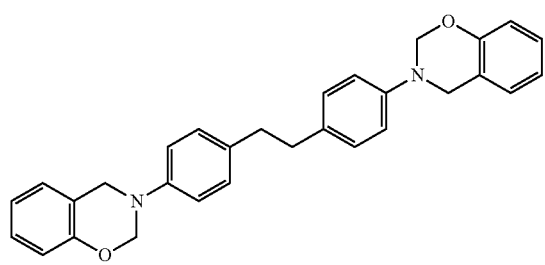
(A2-7)
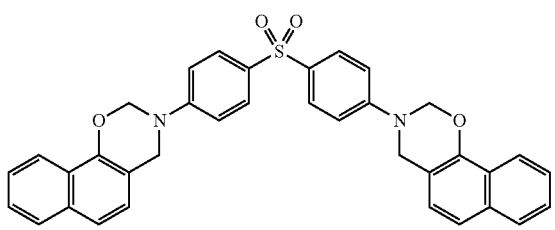

-continued
(A2-8)
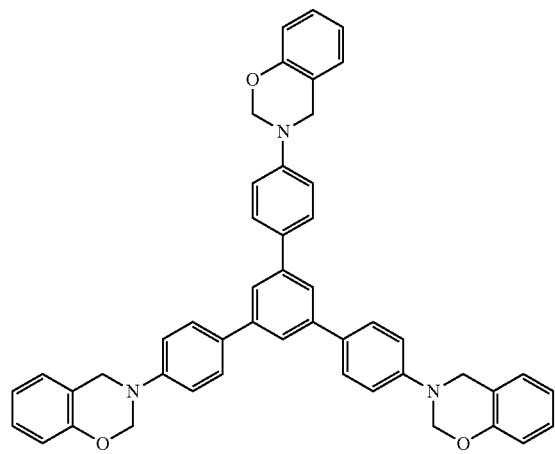
(A2-9)
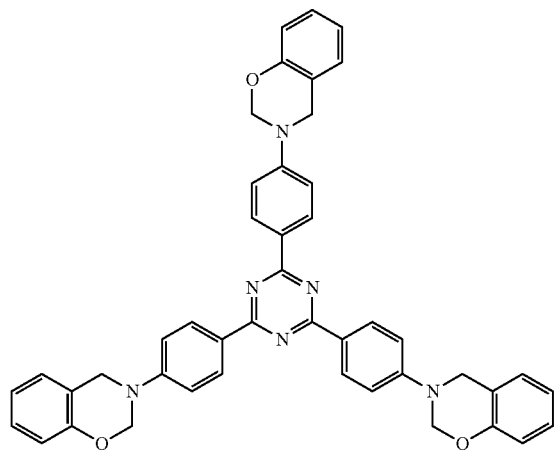
(A2-10)
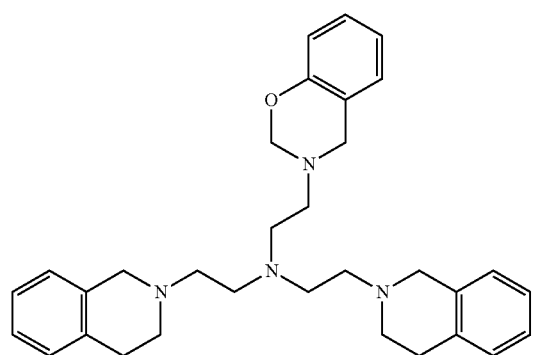
(A2-11)
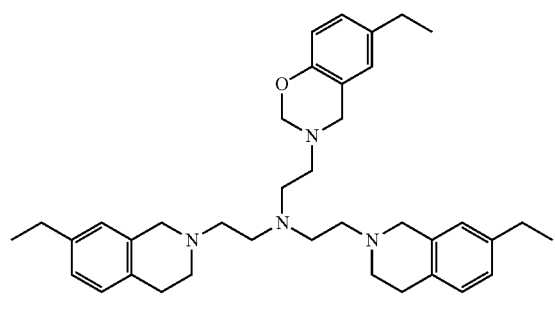
(A2-12)
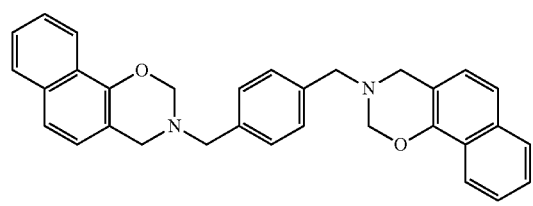
(A2-13)
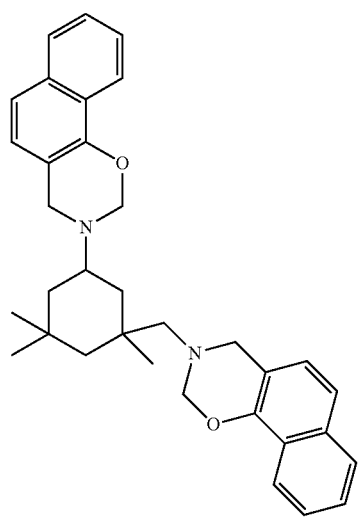

-continued
(A2-14)
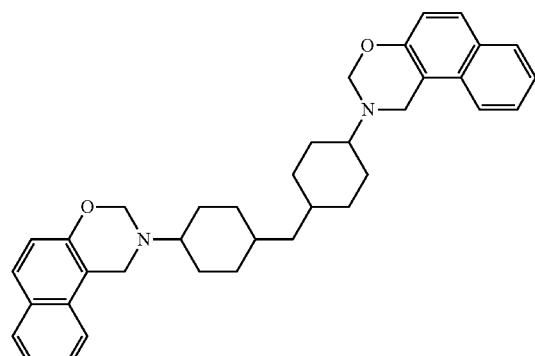
(A2-15)
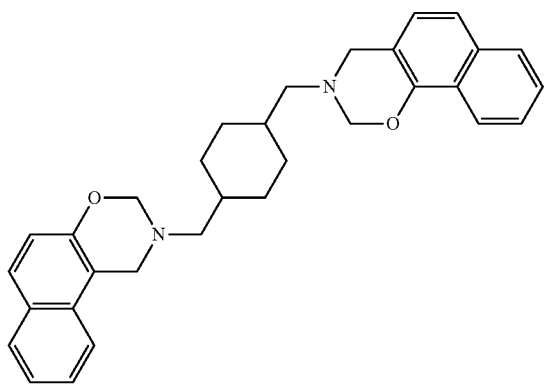
(A2-16)
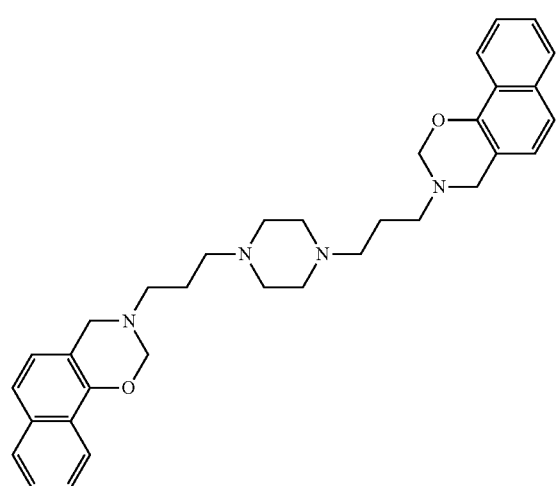
(A2-17)
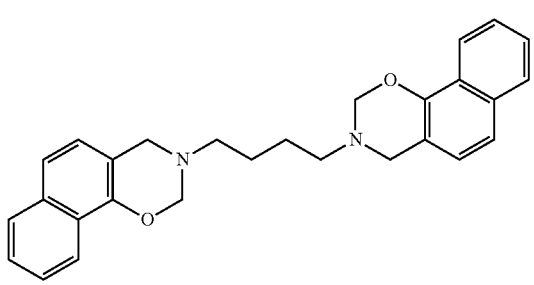
(A2-18)
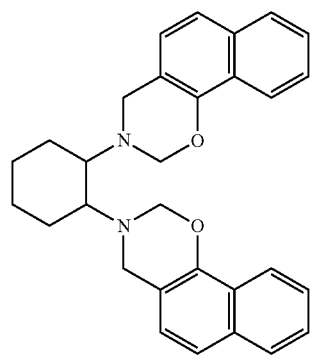
(A2-19)
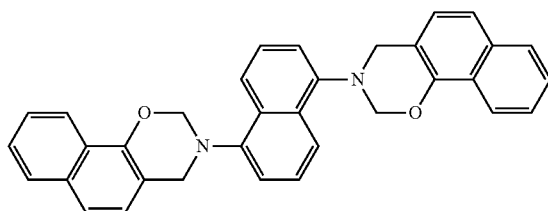
(A2-20)
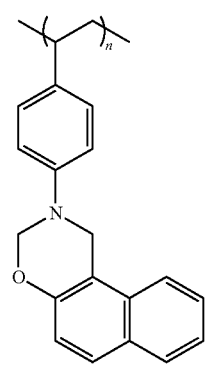

Synthesis Example 1-2-1

Into a reaction vessel equipped with a thermometer, a condenser and a magnetic stirrer were charged 15.0 g of tris(4-aminophenyl)methanol, 14.8 g of paraformaldehyde, 31.9 g of 2-naphthol and 123.2 g of propylene glycol monomethyl ether acetate in a nitrogen atmosphere, and dissolution was permitted. The solution thus obtained was heated to 105° C. to allow for a reaction for 15 hrs.

Methyl isobutyl ketone and water were added to the reaction solution, and extraction by liquid separation was conducted. Thereafter, the organic layer thus obtained was concentrated by using an evaporator, and then reprecipitation was carried out by charging the concentrate into methanol. The precipitate was recovered and then dried to give the compound represented by the above formula (A2-1).

Synthesis Examples 1-2-2 to 1-2-19

The compounds (A2-2) to (A2-19) were synthesized in a similar manner to Synthesis Example 1-2-1 through appropriately selecting the precursors.

Synthesis Example 1-2-20

Into a reaction vessel equipped with a thermometer, a condenser and a magnetic stirrer were charged 10.0 g of poly(4-vinylaniline), 7.5 g of paraformaldehyde, 16.2 g of 2-naphthol and 67.5 g of propylene glycol monomethyl ether acetate in a nitrogen atmosphere, and dissolution was permitted. The solution thus obtained was heated to 105° C. to allow for a reaction for 15 hrs. Methyl isobutyl ketone and water were added to the reaction solution, and extraction by liquid separation was conducted. Thereafter, the organic layer thus obtained was concentrated by using an evaporator, and then reprecipitation was carried out by charging the concentrate into methanol. The precipitate was recovered and then dried to give the compound represented by the above formula (A2-20) which was an aromatic ring-containing vinyl-based resin. The resulting resin (A2-20) had the Mw of 4,500.

Synthesis Example 2-1

Into a 500-mL three-neck flask equipped with a thermometer, a condenser and a magnetic stirrer were charged 250.0 g of m-cresol, 125.0 g of 37% by mass formalin and 2 g of anhydrous oxalic acid in a nitrogen atmosphere, and the reaction was allowed at 100° C. for 3 hrs and at 180° C. for 1 hour. Unreacted monomer was eliminated under a reduced pressure to give a resin represented by the following formula (a-1). The resulting resin (a-1) had the Mw of 11,000.

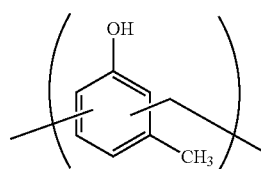

(a-1)

Preparation of Composition for Resist Underlayer Film Formation

The compound (A), the solvent (B), the acid generating agent (C) and the crosslinking agent (D) used in preparation of the composition for resist underlayer film formation are shown below.

(A) Compound

Examples: the compounds (A1-1) to (A1-17), the resin (A1-18), the compounds (A2-1) to (A2-19) and the resin (A2-20) synthesized as described above Comparative Examples: the resin (a-1) synthesized as described above, and compounds represented by the following formulae (a-2) and (a-3)

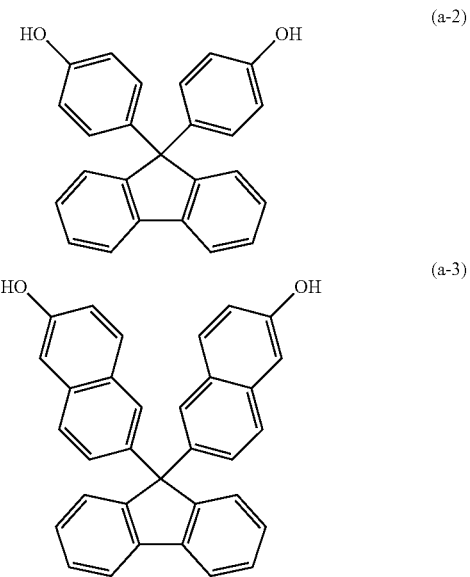

(a-2)

(a-3)

(B) Solvent
B-1: propylene glycol monomethyl ether acetate
B-2: cyclohexanone
(C) Acid Generating Agent
C-1: bis(4-t-butylphenyl)iodonium nonafluoro-n-butanesulfonate (compound represented by the following formula (C-1))

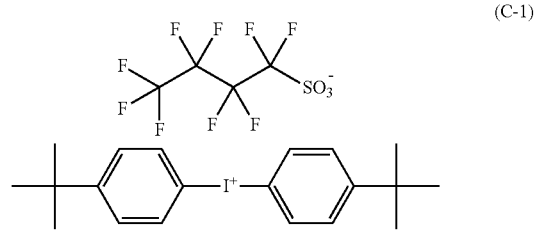

(C-1)

(D) Crosslinking Agent
D-1: 1,3,4,6-tetrakis(methoxymethyl)glycoluril (compound represented by the following formula (D-1))

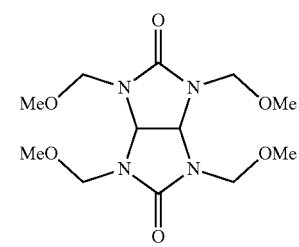

(D-1)

Example 1-1-1

Ten parts by mass of (A1-1) as the compound (A) were dissolved in 90 parts by mass of (B-1) as the solvent (B). The obtained solution was filtered through a membrane filter having a pore size of 0.1 μm to prepare a composition for resist underlayer film formation (J1-1).

Examples 1-1-2 to 1-1-19, 1-2-1 to 1-2-20 and Comparative Examples 1-1 to 1-3

Compositions for resist underlayer film formation (J1-2) to (J1-19), (J2-1) to (J2-20) and (CJ-1) to (CJ-3) were prepared by a similar operation to that of Example 1-1-1 except that the type and the content of each component used were as shown in Tables 1 and 2 below. In Tables 1 and 2, "-" indicates that the corresponding component was not used.

TABLE 1

| | Composition for forming resist underlayer film | (A) Compound type | content (parts by mass) | (B) Solvent type | content (parts by mass) | (C) Acid generating agent type | content (parts by mass) | (D) Crosslinking agent type | content (parts by mass) |
|---|---|---|---|---|---|---|---|---|---|
| Example 1-1-1 | J1-1 | A1-1 | 10 | B-1 | 90 | — | — | — | — |
| Example 1-1-2 | J1-2 | A1-2 | 10 | B-1 | 90 | — | — | — | — |
| Example 1-1-3 | J1-3 | A1-3 | 10 | B-1 | 90 | — | — | — | — |
| Example 1-1-4 | J1-4 | A1-4 | 10 | B-1 | 90 | — | — | — | — |
| Example 1-1-5 | J1-5 | A1-5 | 10 | B-1 | 90 | — | — | — | — |
| Example 1-1-6 | J1-6 | A1-6 | 10 | B-1 | 90 | — | — | — | — |
| Example 1-1-7 | J1-7 | A1-7 | 10 | B-1 | 90 | — | — | — | — |
| Example 1-1-8 | J1-8 | A1-8 | 10 | B-1 | 90 | — | — | — | — |
| Example 1-1-9 | J1-9 | A1-9 | 10 | B-1 | 90 | — | — | — | — |
| Example 1-1-10 | J1-10 | A1-10 | 10 | B-1 | 90 | — | — | — | — |
| Example 1-1-11 | J1-11 | A1-11 | 10 | B-2 | 90 | — | — | — | — |
| Example 1-1-12 | J1-12 | A1-12 | 10 | B-2 | 90 | — | — | — | — |
| Example 1-1-13 | J1-13 | A1-13 | 10 | B-2 | 90 | — | — | — | — |
| Example 1-1-14 | J1-14 | A1-14 | 10 | B-2 | 90 | — | — | — | — |
| Example 1-1-15 | J1-15 | A1-15 | 10 | B-2 | 90 | — | — | — | — |
| Example 1-1-16 | J1-16 | A1-16 | 10 | B-2 | 90 | — | — | — | — |
| Example 1-1-17 | J1-17 | A1-17 | 10 | B-2 | 90 | — | — | — | — |
| Example 1-1-18 | J1-18 | A1-18 | 10 | B-2 | 90 | — | — | — | — |
| Example 1-1-19 | J1-19 | A1-1 | 10 | B-1 | 90 | C-1 | 0.5 | D-1 | 1 |
| Comparative Example 1-1 | CJ-1 | a-1 | 10 | B-1 | 90 | C-1 | 0.5 | D-1 | 3 |

TABLE 2

| | Composition for forming resist underlayer film | (A) Compound type | content (parts by mass) | (B) Solvent Type | content (parts by mass) | (C) Acid generating agent type | content (parts by mass) | (D) Crosslinking agent type | content (parts by mass) |
|---|---|---|---|---|---|---|---|---|---|
| Example 1-2-1 | J2-1 | A2-1 | 10 | B-1 | 90 | — | — | — | — |
| Example 1-2-2 | J2-2 | A2-2 | 10 | B-1 | 90 | — | — | — | — |
| Example 1-2-3 | J2-3 | A2-3 | 10 | B-1 | 90 | — | — | — | — |
| Example 1-2-4 | J2-4 | A2-4 | 10 | B-1 | 90 | — | — | — | — |
| Example 1-2-5 | J2-5 | A2-5 | 10 | B-1 | 90 | — | — | — | — |
| Example 1-2-6 | J2-6 | A2-6 | 10 | B-1 | 90 | — | — | — | — |
| Example 1-2-7 | J2-7 | A2-7 | 10 | B-1 | 90 | — | — | — | — |
| Example 1-2-8 | J2-8 | A2-8 | 10 | B-1 | 90 | — | — | — | — |
| Example 1-2-9 | J2-9 | A2-9 | 10 | B-1 | 90 | — | — | — | — |
| Example 1-2-10 | J2-10 | A2-10 | 10 | B-1 | 90 | — | — | — | — |
| Example 1-2-11 | J2-11 | A2-11 | 10 | B-2 | 90 | — | — | — | — |
| Example 1-2-12 | J2-12 | A2-12 | 10 | B-2 | 90 | — | — | — | — |
| Example 1-2-13 | J2-13 | A2-13 | 10 | B-2 | 90 | — | — | — | — |
| Example 1-2-14 | J2-14 | A2-14 | 10 | B-2 | 90 | — | — | — | — |
| Example 1-2-15 | J2-15 | A2-15 | 10 | B-2 | 90 | — | — | — | — |
| Example 1-2-16 | J2-16 | A2-16 | 10 | B-2 | 90 | — | — | — | — |
| Example 1-2-17 | J2-17 | A2-17 | 10 | B-2 | 90 | — | — | — | — |
| Example 1-2-18 | J2-18 | A2-18 | 10 | B-2 | 90 | — | — | — | — |
| Example 1-2-19 | J2-19 | A2-19 | 10 | B-2 | 90 | — | — | — | — |
| Example 1-2-20 | J2-20 | A2-20 | 10 | B-2 | 90 | — | — | — | — |
| Comparative Example 1-2 | CJ-2 | a-2 | 10 | B-1 | 90 | C-1 | 0.5 | D-1 | 3 |
| Comparative Example 1-3 | CJ-3 | a-3 | 10 | B-1 | 90 | C-1 | 0.5 | D-1 | 3 |

Formation of Resist Underlayer Film

Examples 2-1-1 to 2-1-19, 2-2-1 to 2-2-20 and Comparative Examples 2-1 to 2-3

The compositions for resist underlayer film formation prepared as described above were each applied on a silicon wafer substrate by way of a spin-coating procedure. Thereafter, heating (baking) was carried out at the heating temperature (° C.) for the heating time period (sec) shown in Tables 3 and 4 below in an ambient air atmosphere to form a resist underlayer film having a thickness of 200 nm, whereby substrates having the resist underlayer film formed thereon were obtained. In Table 3, "-" indicates that Comparative Example 2-1 serves as a standard for etching resistance evaluation.

Evaluations

For the compositions for resist underlayer film formation and the substrates provided with a resist underlayer film obtained as described above, the following evaluations were each made according to the following procedures. The results of the evaluations are shown in Tables 3 and 4 below.

Solvent Resistance

The substrate provided with the resist underlayer film obtained as described above was immersed in cyclohexanone (at room temperature) for 1 min. The average film thickness was measured before and after the immersion. The average thickness of the resist underlayer film before the immersion was designated as $X_0$ and the average thickness of the resist underlayer film after the immersion was designated as X, and the absolute value of a numerical value determined according to $(X-X_0) \times 100/X_0$ was calculated and designated as the rate of change of film thickness (%). The solvent resistance was evaluated to be: "A" (favorable) in a case in which the rate of change of film thickness was less than 1%; "B" (somewhat favorable) in a case in which the rate of change of film thickness was no less than 1% and less than 5%; and "C" (unfavorable) in a case in which the rate of change of film thickness was no less than 5%.

Etching Resistance

The resist underlayer film of the substrate provided with the resist underlayer film obtained as described above was treated in an etching apparatus ("TACTRAS" available from Tokyo Electron Limited) under conditions involving: $CF_4$/Ar=110/440 sccm, PRESS.=30 MT, HF RF (radiofrequency power for plasma production)=500 W, LF RF (radiofrequency power for bias)=3,000 W, DCS=-150 V, RDC (flow rate percentage at gas center)=50%, and 30 sec. An etching rate (nm/min) was calculated based on the average thickness of the resist underlayer film before the treatment and the average thickness of the resist underlayer film after the treatment, and the ratio of the etching rate of the resist underlayer film of each Example to the etching rate in Comparative Example 2-1 was calculated as a standard for etching resistance evaluation. The etching resistance was evaluated to be: "A" (extremely favorable) in a case in which the ratio was no less than 0.95 and less than 0.98; "B" (favorable) in a case in which the ratio was no less than 0.98 and less than 1.00; and "C" (unfavorable) in a case in which the ratio was no less than 1.00.

Flatness

Each of the prepared compositions for resist underlayer film formation was applied by a spin-coating procedure using a spin coater ("CLEAN TRACK ACT-12" available from Tokyo Electron Limited), on a silicon substrate 1 provided with a trench pattern having a depth of 100 nm and a groove width of 10 μm formed thereon, as shown in the FIGURE. The rotational speed for the spin coating was the same as that in the case of forming the resist underlayer film having the average thickness of 200 nm in the "Formation of Resist Underlayer Film" described above. Subsequently, the resulting substrate was heated (baked) at 250° C. for 60 sec in an ambient air atmosphere to form a film 2 having an average thickness of 200 nm at parts having been no trench was provided, whereby the silicon substrate having a film formed thereon was obtained, the silicon substrate being covered by the film.

The cross-sectional shape of the silicon substrate having the film formed thereon was observed by using a scanning electron microscope ("S-4800" available from Hitachi High-Technologies Corporation), and the difference (ΔFT) between the height at the center portion of the trench pattern "b" of the resist underlayer film and the height at a position 5 μm away from the edge of the trench pattern, at which no trench pattern was provided "a", was defined as a marker of the flatness. The flatness was evaluated to be "AA" (extremely favorable) in the case of ΔFT being less than 30 nm, "A" (favorable) in the case of ΔFT being no less than 30 nm and less than 40 nm, "B" (somewhat favorable) in the case of ΔFT being no less than 40 nm and less than 60 nm, and "C" (unfavorable) in the case of ΔFT being no less than 60 nm. It is to be noted that the difference in heights shown in the FIGURE is exaggerated.

TABLE 3

| | Composition for forming resist underlayer film | Heating temperature/ heating time period in forming resist underlayer film (° C./sec) | Solvent resistance | Etching resistance | Flatness |
|---|---|---|---|---|---|
| Example 2-1-1 | J1-1 | 250/60 | A | A | A |
| Example 2-1-2 | J1-2 | 250/60 | A | A | A |
| Example 2-1-3 | J1-3 | 250/60 | A | A | A |
| Example 2-1-4 | J1-4 | 250/60 | A | A | A |
| Example 2-1-5 | J1-5 | 250/60 | A | A | AA |
| Example 2-1-6 | J1-6 | 250/60 | A | A | AA |
| Example 2-1-7 | J1-7 | 250/60 | A | A | AA |
| Example 2-1-8 | J1-8 | 250/60 | A | A | A |
| Example 2-1-9 | J1-9 | 250/60 | A | A | A |
| Example 2-1-10 | J1-10 | 250/60 | A | A | A |
| Example 2-1-11 | J1-11 | 250/60 | A | A | A |
| Example 2-1-12 | J1-12 | 250/60 | A | A | A |
| Example 2-1-13 | J1-13 | 250/60 | A | A | A |
| Example 2-1-14 | J1-14 | 250/60 | A | A | A |
| Example 2-1-15 | J1-15 | 250/60 | A | A | A |
| Example 2-1-16 | J1-16 | 250/60 | A | A | AA |
| Example 2-1-17 | J1-17 | 250/60 | A | A | AA |
| Example 2-1-18 | J1-18 | 250/60 | A | A | B |
| Example 2-1-19 | J1-19 | 250/60 | A | A | A |
| Comparative Example 2-1 | CJ-1 | 250/60 | A | — | C |

TABLE 4

| | Composition for forming resist underlayer film | Heating temperature/ heating time period in forming resist underlayer film (° C./sec) | Solvent resistance | Etching resistance | Flatness |
|---|---|---|---|---|---|
| Example 2-2-1 | J2-1 | 250/60 | A | A | AA |
| Example 2-2-2 | J2-2 | 250/60 | A | A | AA |
| Example 2-2-3 | J2-3 | 250/60 | A | A | AA |
| Example 2-2-4 | J2-4 | 250/60 | A | A | AA |
| Example 2-2-5 | J2-5 | 250/60 | A | A | AA |
| Example 2-2-6 | J2-6 | 250/60 | A | A | AA |
| Example 2-2-7 | J2-7 | 250/60 | A | A | AA |
| Example 2-2-8 | J2-8 | 250/60 | A | A | AA |
| Example 2-2-9 | J2-9 | 250/60 | A | A | AA |
| Example 2-2-10 | J2-10 | 250/60 | A | A | A |
| Example 2-2-11 | J2-11 | 250/60 | A | A | A |
| Example 2-2-12 | J2-12 | 250/60 | A | A | A |
| Example 2-2-13 | J2-13 | 250/60 | A | A | A |
| Example 2-2-14 | J2-14 | 250/60 | A | A | A |
| Example 2-2-15 | J2-15 | 250/60 | A | A | A |
| Example 2-2-16 | J2-16 | 250/60 | A | A | A |
| Example 2-2-17 | J2-17 | 250/60 | A | A | A |
| Example 2-2-18 | J2-18 | 250/60 | A | A | A |
| Example 2-2-19 | J2-19 | 250/60 | A | A | A |
| Example 2-2-20 | J2-20 | 250/60 | A | A | B |
| Comparative Example 2-2 | CJ-2 | 250/60 | A | B | C |
| Comparative Example 2-3 | CJ-3 | 250/60 | A | B | C |

As is clear from the results shown in Tables 3 and 4, the compositions for resist underlayer film formation of Examples provided superior flatness, as well as superior solvent resistance and etching resistance. To the contrary, the compositions for resist underlayer film formation of Comparative Examples provided inferior flatness, and also provided the film exhibiting poor performances in solvent resistance and etching resistance.

The composition for resist underlayer film formation of the one embodiment of the present invention is capable of forming a resist underlayer film having superior flatness, and being superior in both solvent resistance and etching resistance. The resist underlayer film of the another embodiment of the present invention has superior flatness, and is superior in both solvent resistance and etching resistance. The method for resist underlayer film formation of the yet another embodiment of the invention enables a resist underlayer film having superior flatness to be formed. The production method of a patterned substrate of the still another embodiment of the invention enables a substrate having a favorable pattern configuration to be obtained by using a superior resist underlayer film formed as described above. Therefore, these can be suitably used for manufacture, etc., of semiconductor devices in which further progress of microfabrication is expected in the future.

Obviously, numerous modifications and variations of the present invention are possible in light of the above teachings. It is therefore to be understood that within the scope of the appended claims, the invention may be practiced otherwise than as specifically described herein.

What is claimed is:

1. A composition for resist underlayer film formation, comprising:
a resin comprising at least one oxazine structure fused to an aromatic ring; and
a solvent,
wherein the resin comprises a partial structure represented by formula (1):

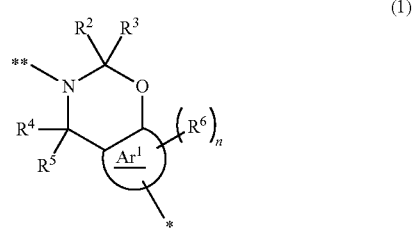

(1)

wherein, in the formula (1),
$R^2$ to $R^5$ each independently represent a hydrogen atom or a monovalent organic group having 1 to 20 carbon atoms;
$Ar^1$ represents a group obtained by removing (n+3) or (n+2) hydrogen atoms on the aromatic ring from an arene having 6 to 20 carbon atoms;
$R^6$ represents a hydroxy group, a halogen atom, a nitro group or a monovalent organic group having 1 to 20 carbon atoms;
n is an integer of 0 to 9, wherein in a case in which n is no less than 2, a plurality of $R^6$s are identical or different, or wherein two or more of the plurality of $R^6$s taken together represent a ring structure having 4 to 20 ring atoms together with the carbon chain to which the two or more of the plurality of $R^6$s bond; and
* and ** each independently denote a bonding site to a part other than the partial structure represented by the formula (1) in the resin.

2. The composition according to claim 1, wherein the resin comprises a group represented by formula (1-1), a group represented by formula (1-2), or a combination thereof:

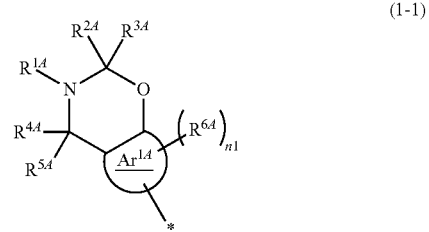

(1-1)

wherein, in the formula (1-1),
$R^{1A}$ represents a monovalent organic group having 1 to 20 carbon atoms;
$R^{2A}$ to $R^{5A}$ each independently represent a hydrogen atom or a monovalent organic group having 1 to 20 carbon atoms;
$Ar^{1A}$ represents a group obtained by removing (n1+3) or (n1+2) hydrogen atoms on the aromatic ring from an arene having 6 to 20 carbon atoms;
$R^{6A}$ represents a hydroxy group, a halogen atom, a nitro group or a monovalent organic group having 1 to 20 carbon atoms;
n1 is an integer of 0 to 9, wherein in a case in which n1 is no less than 2, a plurality of $R^{6A}$s are identical or different, or wherein two or more of the plurality of $R^{6A}$s taken together represent a ring structure having 4 to 20 ring atoms together with the carbon chain to which the two or more of the plurality of $R^{6A}$s bond; and

** denotes a bonding site to a part other than the group represented by the formula (1-1) in the resin,

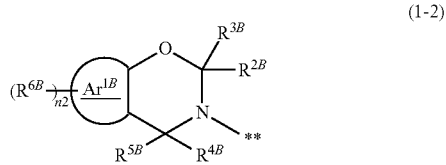
(1-2)

wherein, in the formula (1-2), $R^{2B}$ to $R^{5B}$ each independently represent a hydrogen atom or a monovalent organic group having 1 to 20 carbon atoms;

$Ar^{1B}$ represents a group obtained by removing (n2+2) hydrogen atoms on the aromatic ring from an arene having 6 to 20 carbon atoms;

$R^{6B}$ represents a hydroxy group, a halogen atom, a nitro group or a monovalent organic group having 1 to 20 carbon atoms;

n2 is an integer of 0 to 10, wherein in a case in which n2 is no less than 2, a plurality of $R^{6B}$s are identical or different, or wherein two or more of the plurality of $R^{6B}$s taken together represent a ring structure having 4 to 20 ring atoms together with the carbon chain to which two or more of the plurality of $R^{6B}$s bond; and

** denotes a bonding site to a part other than the group represented by the formula (1-2) in the resin.

3. The composition according to claim 2, wherein the resin comprises a plurality of groups represented by the formula (1-1), a plurality of groups represented by the formula (1-2), or a combination thereof.

4. A production method of a patterned substrate comprising:

applying the composition for resist underlayer film formation according to claim 3 directly or indirectly on a substrate to obtain a coating film;

heating the coating film to obtain a resist underlayer film;

forming a resist pattern directly or indirectly on the resist underlayer film; and carrying out etching with the resist pattern used as a mask.

5. A production method of a patterned substrate comprising:

applying the composition for resist underlayer film formation according to claim 2 directly or indirectly on a substrate to obtain a coating film;

heating the coating film to obtain a resist underlayer film;

forming a resist pattern directly or indirectly on the resist underlayer film; and carrying out etching with the resist pattern used as a mask.

6. The composition according to claim 1, wherein a content of the resin in the composition is no less than 1% by mass and no greater than 50% by mass.

7. A production method of a patterned substrate comprising:

applying the composition for resist underlayer film formation according to claim 6 directly or indirectly on a substrate to obtain a coating film;

heating the coating film to obtain a resist underlayer film;

forming a resist pattern directly or indirectly on the resist underlayer film; and carrying out etching with the resist pattern used as a mask.

8. A production method of a patterned substrate comprising:

applying the composition for resist underlayer film formation according to claim 1 directly or indirectly on a substrate to obtain a coating film;

heating the coating film to obtain a resist underlayer film;

forming a resist pattern directly or indirectly on the resist underlayer film; and carrying out etching with the resist pattern used as a mask.

* * * * *